United States Patent
Van Veen et al.

(10) Patent No.: US 7,570,063 B2
(45) Date of Patent: Aug. 4, 2009

(54) SPACE-TIME MICROWAVE IMAGING FOR CANCER DETECTION

(75) Inventors: Barry D. Van Veen, McFarland, WI (US); Susan C. Hagness, Madison, WI (US); Essex Julian Bond, Madison, WI (US); Xu Li, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1196 days.

(21) Appl. No.: 10/190,352

(22) Filed: Jul. 3, 2002

(65) Prior Publication Data

US 2003/0088180 A1    May 8, 2003

Related U.S. Application Data

(60) Provisional application No. 60/303,461, filed on Jul. 6, 2001.

(51) Int. Cl.
    *G01R 27/32* (2006.01)
(52) U.S. Cl. .................. 324/637; 324/638; 600/407; 600/408; 600/430
(58) Field of Classification Search ............... 600/407, 600/408, 430; 606/27–52; 607/154–156, 607/101; 324/637–648
See application file for complete search history.

(56) References Cited

U.S. PATENT DOCUMENTS 5,016,018 A * 5/1991 Chang et al. ............... 342/351
5,363,050 A * 11/1994 Guo et al. .................. 324/638
5,570,691 A * 11/1996 Wright et al. .............. 600/447
5,704,355 A * 1/1998 Bridges ...................... 600/407
5,706,013 A   1/1998 Melvin et al.
5,807,257 A * 9/1998 Bridges ...................... 600/430
5,829,437 A * 11/1998 Bridges ...................... 600/430

(Continued)

OTHER PUBLICATIONS

Barry Van Veen, "Minimum Variance Beamforming," in Adaptive Radar Detection and Estimation, Eds. Haykin and A. Steinhardt, John Wiley & Sons, New York, Chapter 4, Mar. 1992, pp. 161-236.

(Continued)

*Primary Examiner*—Brian L. Casler
*Assistant Examiner*—Sanjay Cattungal
(74) *Attorney, Agent, or Firm*—Foley & Lardner LLP

(57) ABSTRACT

Microwave imaging via space-time beamforming is carried out by transmitting microwave signals from multiple antenna locations into an individual to be examined and receiving the backscattered microwave signals at multiple antenna locations to provide received signals from the antennas. The received signals are processed in a computer to remove the skin interface reflection component of the signal at each antenna to provide corrected signal data. The corrected signal data is provided to a beamformer process that time shifts the received signals to align the returns from a scatterer at a candidate location, and then passes the time aligned signals through a bank of filters, the outputs of which are summed, time-gated and the power therein calculated to produce the beamformer output signal at a candidate location. The beamformer is then scanned to a plurality of different locations in the individual by changing the time shifts, filter weights and time-gating of the beamformer process. The output power may be displayed as a function of scan location, with regions of large output power corresponding to significant microwave scatterers such as malignant lesions.

46 Claims, 11 Drawing Sheets

U.S. PATENT DOCUMENTS

| | | | |
|---|---|---|---|
| 5,942,899 A * | 8/1999 | Shrekenhamer et al. | 324/326 |
| 6,005,916 A * | 12/1999 | Johnson et al. | 378/87 |
| 6,061,589 A * | 5/2000 | Bridges et al. | 600/430 |
| 6,064,903 A | 5/2000 | Riechers et al. | |
| 6,091,361 A | 7/2000 | Davis et al. | |
| 6,157,697 A | 12/2000 | Mertelmeier et al. | |
| 6,161,034 A * | 12/2000 | Burbank et al. | 600/431 |
| 6,163,726 A | 12/2000 | Wolf | |
| 6,348,898 B1 | 2/2002 | Rosenbury et al. | |
| 6,421,550 B1 * | 7/2002 | Bridges et al. | 600/407 |
| 6,448,788 B1 * | 9/2002 | Meaney et al. | 324/637 |
| 7,061,970 B2 | 6/2006 | Reed et al. | |
| 7,454,242 B2 | 11/2008 | Fear et al. | |
| 2002/0061280 A1 * | 5/2002 | Mattrey | 424/9.52 |
| 2002/0163480 A1 * | 11/2002 | Eiges | 343/911 L |
| 2002/0197209 A1 * | 12/2002 | Mattrey | 424/1.11 |
| 2003/0088180 A1 | 5/2003 | Van Veen et al. | |
| 2005/0251018 A1 * | 11/2005 | Gleman | 600/407 |
| 2005/0259621 A1 | 11/2005 | Lee | |
| 2006/0058606 A1 * | 3/2006 | Davis et al. | 600/407 |
| 2006/0183995 A1 | 8/2006 | Bond et al. | |
| 2007/0282200 A1 | 12/2007 | Johnson et al. | |

OTHER PUBLICATIONS

Susan C. Hagness, et al., "Two-Dimensional FDTD Analysis of a Pulsed Microwave Confocal System for Breast Cancer Detection: Fixed-Focus and Antenna-Array Sensors," IEEE Trans. Biomed. Eng., vol. 45, No. 12, Dec. 1998, pp. 1470-1479.

Susan C. Hagness, et al., "Three-Dimensional FDTD Analysis of a Pulsed Microwave Confocal System for Breast Cancer Detection: Design of an Antenna-Array Element," IEEE Trans. Antennas and Propagation, vol. 47, No. 5, May 1999, pp. 783-791.

Xu Li, et al., "A Confocal Microwave Imaging Algorithm for Breast Cancer Detection," IEEE Microwave and Wireless Components Letters, vol. 11, No. 3, Mar. 2001, pp. 130-132.

Elise C. Fear, et al., "Enhancing Breast Tumor Detection with Near-Field Imaging," IEEE Microwave Magazine, Mar. 2002, pp. 48-56.

X. Li, E.J. Bond, D. Hagl, B. Van Veen, S.C. Hagness, and J.H. Booske, "Microwave Breast Cancer Detection Using Ultrawideband Space-Time Focusing Techniques," IEEE Antennas and Propagation Society International Symposium and USNC/URSI National Radio Science Meeting, Boston, MA, Jul. 8-13, 2001.

Essex J. Bond, Xu Li, Barry D. Van Veen, and Susan C. Hagness, "Space-Time Microwave Imaging for Breast Cancer Detection," Progress in Electromagnetic Research Symposium, Osaka, Japan, Jul. 18-22, 2001.

Essex J. Bond, Xu Li, Susan C. Hagness, and Barry D. Van Veen, "Microwave Imaging Via Space-Time Beamforming for Early Detection of Breast Cancer," IEEE International Conference on Acoustics, Speech, and Signal Processing, Orlando, Florida, May 2002.

X. Li, E.J. Bond, S.C. Hagness, B.D. Van Veen, and D. van der Weide, "Three-Dimensional Microwave Imaging Via Space-Time Beamforming for Breast Cancer Detection," IEEE Antennas and Propagation Society International Symposium and USNC/URSI Radio Science Meeting, San Antonio, Texas, Jun. 2002.

Xu Li, Essex J. Bond, Susan C. Hagness, and Barry D. Van Veen, "Robustness of Space-Time Microwave Imaging to Breast Tissue Dielectric Properties," Progress in Electromagnetic Research Symposium, Cambridge, MA, Jul. 2002.

* cited by examiner

SPACE-TIME MICROWAVE IMAGING FOR CANCER DETECTION

CROSS-REFERENCE TO RELATED APPLICATION

This application claims the benefit of provisional application No. 60/303,461, filed Jul. 6, 2001, the disclosure of which is incorporated herein by reference.

REFERENCE TO GOVERNMENT RIGHTS

This invention was made with United States government support awarded by the following agencies: NSF 9900280. The United States government has certain rights in this invention.

FIELD OF THE INVENTION

The present invention pertains generally to the field of medical imaging and particularly to microwave imaging of tissue for the detection and location of tumors.

BACKGROUND OF THE INVENTION

Various imaging techniques have been employed for detecting and locating cancerous tumors in body tissue. X-ray and ultrasound imaging techniques are commonly utilized in screening for breast cancer. X-ray mammography is the most effective current method for detecting early stage breast cancer. However, X-ray mammography suffers from relatively high false positive and false negative rates, requires painful breast compression, and exposes the patient to low levels of ionizing radiation.

Microwave based imaging methods have been proposed for use in imaging of breast tissue and other body tissues as an alternative to current ultrasound and X-ray imaging techniques. Microwave imaging does not require breast compression, does not expose the patient to ionizing radiation, and can be applied at low power levels. Microwave-based imaging exploits the large contrast in dielectric properties between normal and malignant tissue. With microwave tomography, the dielectric-properties profile of an object being imaged is recovered from measurement of the transmission of microwave energy through the object. This approach requires the solution of an ill-conditioned nonlinear inverse-scattering problem which requires elaborate image reconstruction algorithms. An alternative microwave imaging approach is based on backscatter methods that use the measured reflected signal to infer the locations of significant sources of scattering in the object being imaged, and are simpler to implement and more robust. Backscatter methods require the focusing of the received signal in both space and time to discriminate against clutter and to obtain acceptable resolution. This may be accomplished with an antenna array and ultra-wideband microwave probe signals. For a discussion of this approach, see, S. C. Hagness, et al., "Two-Dimensional FDTD Analysis of a Pulsed Microwave Confocal System for Breast Cancer Detection: Fixed Focus and Antenna-Array Sensors," IEEE Trans. Biomed. Eng., Vol. 45, December, 1998, pp. 1470-1479; S. C. Hagness, et al., "Three-Dimensional FDTD Analysis of a Pulsed Microwave Confocal System for Breast Cancer Detection: Design of an Antenna-Array Element," IEEE Trans. Antennas and Propagation, Vol. 47, May, 1999, pp. 783-791; S. C. Hagness, et al., "Dielectric Characterization of Human Breast Tissue and Breast Cancer Detection Algorithms for Confocal Microwave Imaging," Proc. of the $2^{nd}$ World Congress on Microwave and Radio Frequency Processing, Orlando, Fla., April, 2000; and X. Li, et al., "A Confocal Microwave Imaging Algorithm for Breast Cancer Detection," IEEE Microwave and Wireless Components Letters, Vol. 11, No. 3, March, 2001, pp. 130-132.

SUMMARY OF THE INVENTION

Space-time microwave imaging in accordance with the invention overcomes many of the limitations of conventional breast cancer screening modalities. Of particular significance, microwave imaging via space-time (MIST) beam-forming has the potential to reduce the number of false negatives currently associated with conventional X-ray mammography. MIST exploits the significant dielectric-properties contrast between malignant and normal breast tissue at microwave frequencies by taking advantage of the exceptionally strong biophysical contrast mechanisms of clinical interest, such as water content, vascularization/angiogenesis, blood flow rate, and temperature. MIST techniques in accordance with the invention have the potential for sensitivity and resolution sufficient to allow reliable detection of extremely small (millimeter size) malignant tumors even in radiographically dense breast tissue or in the upper outer breast quadrant near the chest wall. In addition, MIST utilizes non-ionizing microwave radiation, is noninvasive, does not require the injection of contrast agents, and avoids the need for breast compression. The present invention also has the potential to reduce the number of false positives associated with conventional X-ray mammography and thereby reduce the number of unnecessary biopsies. Because low-power microwave exposure is harmless, MIST exams may be done more frequently than X-ray mammography, and monitoring and comparison of breast scans from one exam to the next can be used to identify changes in lesions due to vascularization and the growth of cancerous tissue. Further, discrimination between malignant and benign tumors may also be possible based on spectral and polarization characteristics of benign and malignant tumors. MIST may be implemented utilizing relatively low-cost hardware, allowing reduced cost screening procedures and allowing routine screening to be made more widely available to medically under-served populations in both developed and underdeveloped countries. Further, the safety of MIST imaging techniques, the comfort of the procedure (no breast compression required), the ease of use, and the low cost of the scanning procedure should help to improve acceptance by the public of regular (e.g., annual) screenings. The present invention further provides significantly improved imaging over prior microwave imaging approaches using a single antenna with no spatial focusing or using an array of antennas with simple spatial focusing via time shift and summing of backscattered waveforms.

The space-time microwave imaging system of the invention preferably carries out processing to remove the effect of artifacts such as the skin response or the antenna response from the data before beam former processing. The artifact removal process estimates the artifact component of the signal at each antenna in an array of antennas as a filtered combination of the signals at all other antennas. The filter weights are chosen to minimize the residual signal over that portion of the received data dominated by the artifact.

The beam forming processing preferably first time shifts the received signals from the antennas after artifact removal to approximately align the returns from a scatterer at a candidate location. The time-aligned signals are passed through a bank of filters (e.g., finite-impulse response filters for time domain processing), one for each antenna channel, with the outputs of the filters then summed and time gated and the power calculated to produce the beamformer output signal at a candidate location. The filters may be designed using a least squares technique to present maximum gain (e.g., unit gain) to scattered signals originating from the candidate location. The beamformer output power thus represents an estimate of the energy scattered by that location. The beamformer process is then scanned to a plurality of different locations in the individual (e.g., in the breast) by changing the time shifts, filter weights, and time gating in the beamformer process. The output power may then be displayed as a function of scan location, with regions of large output power corresponding to significant microwave scatterers (e.g., malignant lesions). Processing may further be carried out to account for the effect of frequency dependent scattering. Scattering is frequency dependent due to dispersive dielectric properties and the presence of multiple scattering surfaces. Errors due to frequency dependent scattering may be compensated by processing the beamformer output signal prior to time gating using parametric signal processing models for frequency dependent scattering effects.

The present invention may also be utilized to carry out hyperthermia treatment of a detected lesion by applying signals to the antennas in the array with appropriate weights focus the microwave radiation from the antennas onto the detected position of the lesion.

A space-time microwave imaging system that carries out imaging in accordance with the invention includes an array of antennas for radiating and receiving microwaves, a microwave source connected to the array of antennas to provide microwave signals such as pulse signals of a selected width and repetition rate to the antennas, and a receiver connected to the antennas to detect the microwave signals received by the antennas and provide signal data corresponding thereto. The system of the invention may also utilize a microwave source which provides discrete frequency signals that can be combined to provide the effect of a broadband pulse source. A computer is connected to receive the signal data and to carry out beamformer processing. The computer is also preferably programmed to estimate an artifact reflection component of a signal at each antenna as a filtered combination of the signals at all other antennas and to subtract the estimated artifact reflection component from the signal data to provide corrected signal data. The weights of the filters are chosen to minimize a residual signal over that portion of the received data dominated by the reflection. The computer is programmed to process the corrected signal data in a beamformer process to time shift the corrected signal data to approximately align the returns from a scatterer at a candidate location. The time aligned signals are passed through a bank of filters with a filter for each antenna, the outputs of the filters are summed to form a summed signal, and the power in the summed signal is calculated to produce a beamformer output signal. The beamformer filters are designed to present maximum gain to scattered signals originating from the candidate location. The beamformer process is scanned to a plurality of different candidate locations in the object to be imaged, such as a portion of an individual, by changing the time shifts and filter weights to generate multi-dimensional output data. An output device such as a cathode ray tube, LCD screen, etc. may be connected to the computer to display the multi-dimensional output power as a function of scanned locations, providing an image on which cancerous lesions may be distinguished from surrounding tissue. The computer may be further programmed to time gate the summed signal to form a time-gated summed signal and to calculate the power in the time-gated summed signal. The beamformer process can be scanned in the object by changing the time shifts, filter weights and time gates to generate the multi-dimensional output power data. The computer may be further programmed to process the beamformer output signal from the filters prior to time gating using a parametric signal processing model to compensate frequency dependent scattering effects. The computer may be further programmed in the beamformer process to apply a selected window to the time aligned signals before passing the time aligned signals through a bank of filters, and to apply a selected window to the summed signal before the power in the summed signal is calculated, to reduce the effects of clutter in the signal. The beamformer filters are preferably FIR filters designed to satisfy a penalized least squares condition to present unit gain to scattered signals originating from a candidate location. To increase the signal to clutter ratio, the system may include signal processing circuitry that receives the pulses from the microwave source and passes the pulses through a delay and a filter for each antenna before providing the delayed and filtered pulses to the antennas. The delays and filters for each antenna are selected to focus the radiated microwave energy from the array of antennas at a selected candidate location in the object. At sufficiently high power levels, such focussing may also be utilized to provide hyperthermia treatment at a location which has been previously identified as a tumor.

Further objects, features and advantages of the invention will be apparent from the following detailed description when taken in conjunction with the accompanying drawings.

DETAILED DESCRIPTION OF THE INVENTION

Figure 1:
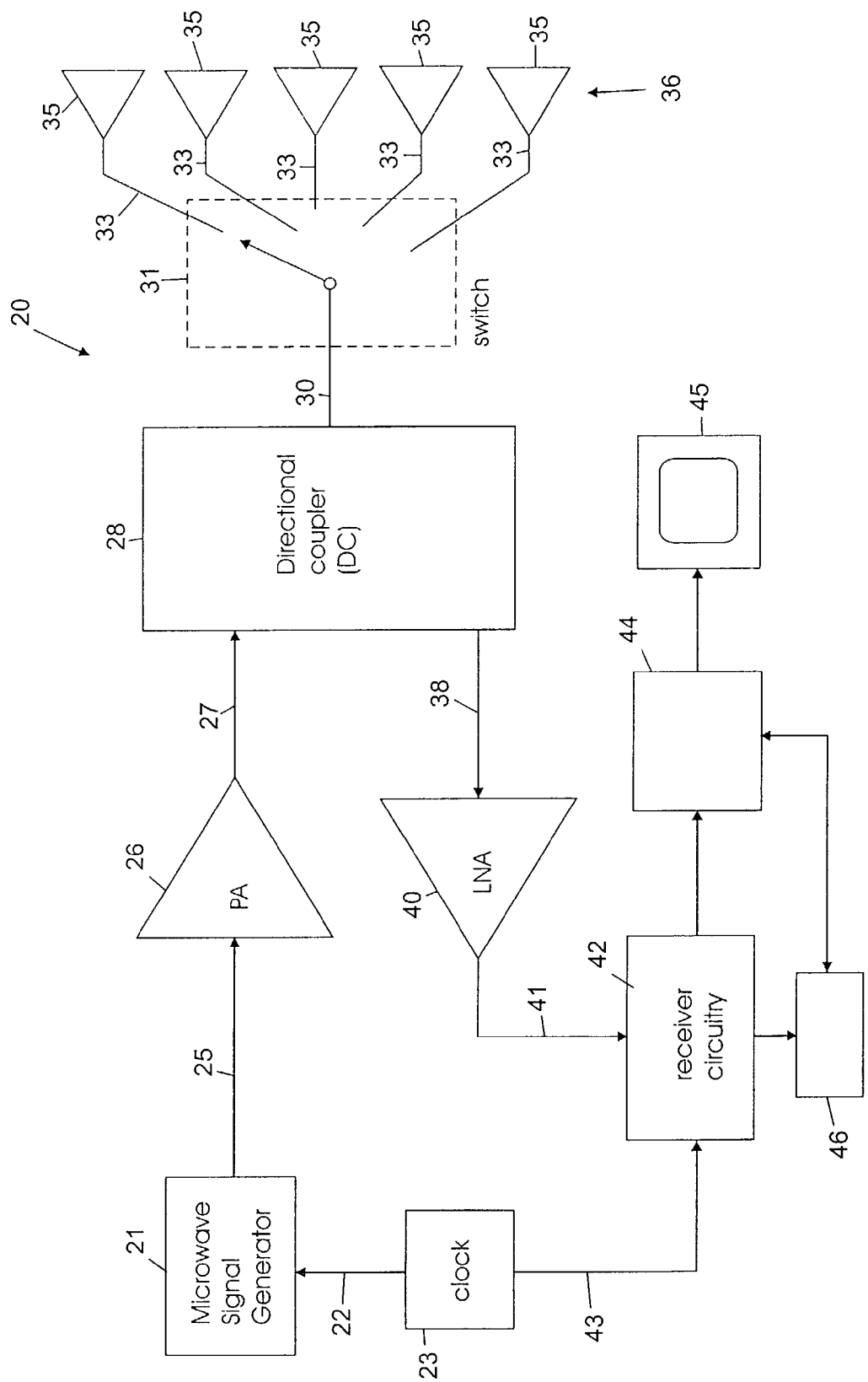
FIG. 1 is a block diagram of a space-time microwave imaging system in accordance with the invention for transmitting and receiving using the same antenna.

In one embodiment for carrying out space-time microwave imaging (MIST) in accordance with the invention, each antenna in an array of antennas sequentially transmits a low-power ultra-short microwave pulse into an object to be imaged, such as the breast, and collects the backscatter signal. The relative arrival times and amplitudes of backscattered signals received by the antennas across the antenna array provide information that can be used to detect the presence and determine the location of malignant lesions. Breast carcinomas act as significant microwave scatterers because of the large dielectric-properties contrast with the surrounding tissue. The problem of detecting and localizing scattering objects using pulsed signals and antenna arrays is similar to that encountered in radar systems, such as those used for air traffic control, military surveillance, and land-mine detection.

Data in published literature and from our measurements on freshly excised breast biopsy tissue suggest that the malignant-to-normal breast tissue contrast in dielectric constant, $\in_r$, and conductivity, $\sigma$, is between 2:1 and 10:1, depending on the density of the normal tissue. The higher dielectric properties of malignant breast tissue arise, in part, from increased protein hydration and a breakdown of cell membranes due to necrosis. The contrast ratio does not vary significantly with tumor age, which suggests the potential for detecting tumors at the earliest stages of development. Microwaves offer exceptionally high contrast compared to other imaging modalities, such as X-ray mammography, which exploit intrinsic contrasts on the order of a few percent. Measurements suggest typical attenuation is less than 4 dB/cm up through 10 GHz, indicating that commercial microwave instrumentation with 100 dB of dynamic range is capable of imaging through 25 cm of tissue. MIST uses microwave pulses that are on the order of 100 ps in duration, with peak powers on the order of a few milliwatts—approximately $\frac{1}{100}^{th}$ of the power of a typical cellular phone. Assuming a pulse repetition frequency of 1 MHz and a maximum scan depth of 10 cm, an array of 100 antennas could be sequentially scanned in 0.1 seconds.

The goal of conventional microwave tomography is the recovery of the dielectric-properties profile of an object from measurement of the transmission and scattering of microwave energy through the object. In contrast, MIST in accordance with the invention need be carried out only to identify the presence and location of strong scatterers in the breast by directly imaging backscattered signal power. Consequently, MIST avoids the need to solve a challenging, ill-conditioned nonlinear inverse-scattering problem. Early active microwave backscatter techniques were unsuccessful because they used a single antenna location for transmitting and receiving and thus had no possibility of spatially focusing the backscattered signal. The use of an antenna array and short pulses enables MIST to focus in both space and time. Thus, MIST significantly enhances the response from malignant lesions while minimizing clutter signals, thereby overcoming challenges presented by breast heterogeneity and enabling the detection of lesions as small as 1-2 mm. Note that resolution is not determined by the wavelength of the microwave excitation. Rather, the spatial extent of the array aperture measured in wavelengths and the temporal duration of the pulse are the dominant factors in determining the resolution limit.

Preliminary measurements suggest that the contrast between the dielectric properties of normal breast tissue and many benign lesions is negligible, in which case benign lesions would not act as strong microwave scatterers, allowing discrimination of benign and cancerous lesions. Furthermore, in contrast to conventional microwave tomography, MIST can also exploit morphology-dependent characteristics of lesions, such as spectral and polarization signatures, as well as the enhanced backscatter due to vascularization of malignant tumors, to further distinguish cancerous lesions from other scattering structures. In addition, change in lesion size is reflected in the backscattered spectral characteristics and signal-to-clutter ratio.

An exemplary space-time microwave imaging system in accordance with the invention which provides transmission and reception with the same antenna is shown generally at 20 in FIG. 1. The imaging system 20 includes a microwave signal generator 21 which is supplied, on a line 22, with clock pulses from a clock 23. The output of the signal generator 21, which as described below may be short broadband pulses or a signal synthesized from multiple discrete frequencies, is provided on a line 25 to a power amplifier 26, the output of which is provided on a line 27 to a directional coupler 28. The output of the directional coupler 28 is provided on a line 30 to a switching system 31 which selectively directs the power from the line 30 to lines 33 leading to each of the antennas 35 which are arranged in an array 36 of antennas (e.g., a rectangular or circular array). An array of antennas may be effectively provided by using one antenna 35 and moving it from position to position to collect data at each position, although the forming of a "virtual" array in this manner is not preferred. Further, the array may be formed to partially surround the object being imaged, for example, for use in breast imaging the array may formed to encircle the pendant breast. The antennas 35 and other microwave components should be wideband and preferably operate in the 1-10 GHz range. Examples of wideband antenna designs that may be utilized are the "bowtie" and Vivaldi type antennas and horn antennas designed for wideband operation. The switch 31 is formed to selectively provide a pulse of microwave power individually to the antennas 35 from the directional coupler 28 and to receive a signal from that antenna which is directed back through the switch 31 to the directional coupler 28. The directional coupler 28 sends the received signal on a line 38 to a low noise amplifier 40, the output of which is provided on a line 41 to a receiver 42. The receiver 42 also receives clock pulses on a line 43 from the clock 23. The clock pulses on the line 43 allow the receiver 42 to time the onset of pulses of microwave power supplied from the signal generator 21 to allow correlation in time of the received signal with respect to the transmitted signal. Alternatively, the power output from the signal generator 21 may be provided through a power splitter to the receiver 42 to allow time correlation. The signal generator 21, which may include a computer or digital processor, generates appropriately timed and shaped output pulses, discrete frequencies, etc., as required for the type of microwave transmission being utilized. The receiver 42 may be of conventional construction, providing detection of the received microwave signal and conversion of the detected signal to digitized data, e.g., with sampling of the received signal after each pulse to build up a digitized waveform, with the digitized data being provided to a digital signal processor of conventional design within the receiver 42 or to an appropriately programmed computer 44 (e.g., a general purpose PC, a dedicated digital signal processor, etc.) all of which will be referred to herein generally as a "computer." It is understood that any type of computer that can be programmed to carry out the signal/data processing set forth herein may be utilized. The receiver 42 or the separate computer 44 processes the data to provide image data which may be displayed on a display device 45, such as a video display terminal, or which may be transmitted to a recording device 46 such as a magnetic disk or CD ROM for long-term storage, or transmitted for printout, further data processing, etc. In accordance with the invention, space-time beamforming is carried out in a computer in the receiver 42 or a separate computer 44 on the data received from the antennas, as described further below. Further, signal processing is preferably employed to carry out a reflection artifact subtraction process (e.g., for the skin interface response or the antenna response) to reduce the effect of the artifact response on the received image data. Signal processing may also be carried out to compensate for frequency dependent scattering. As an example only of commercial instruments that may be utilized, the signal generator 21, amplifiers 26 and 40, directional coupler 28, receiver 42 and clock 23 may be implemented in an Agilent Vector Network Analyzer model 8720 ES, particularly for the discrete frequency based approach, and the computer 44 may be connected to control the signal generator 21 and the switch 31.

Figure 2:
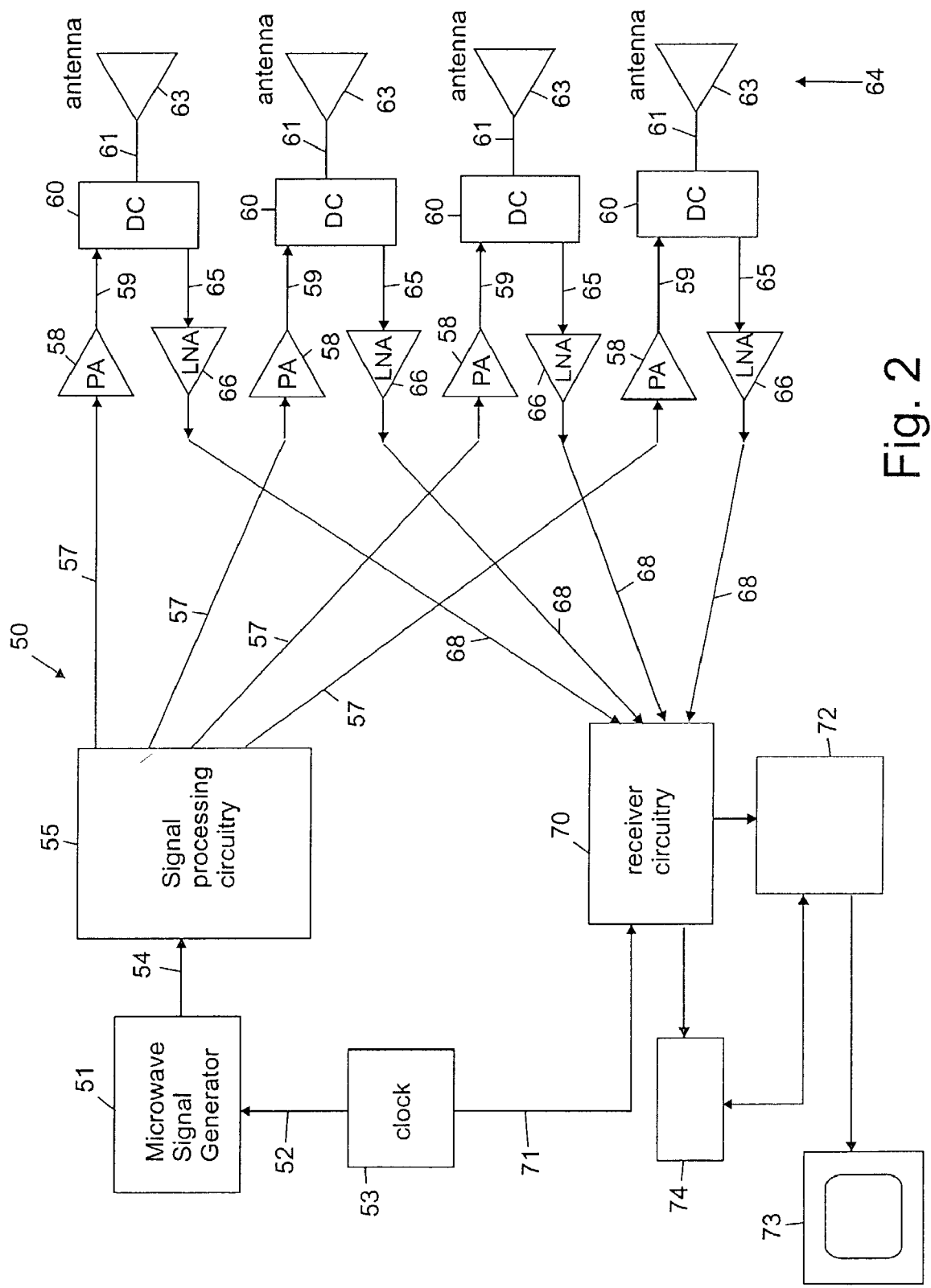
FIG. 2 is a block diagram of a further embodiment of a space-time microwave imaging system in accordance with the invention providing simultaneous transmission and reception with all antennas.

A space-time microwave imaging system in accordance with the invention which may be utilized for simultaneous transmission from each antenna is shown generally at 50 in FIG. 2. The system 50 includes a signal generator 51 which receives a clock pulse on a line 52 from a clock 53. The output of the signal generator 51 is provided on a line 54 to signal processing circuitry 55 which distributes the microwave (e.g., pulse) output on lines 57 to power amplifiers 58. Each of the power amplifiers 58 provides its output on a line 59 to a directional coupler 60, the output of which is provided on a line 61 to an individual antenna 63. The antennas 63 are arranged to form an array 64 of antennas, e.g., a rectangular array of antennas arranged in rows and columns. The signal processing circuitry 55 distributes the pulse of microwave on each of its output lines 57 with frequency dependent filtering to provide the desired microwave radiation from the antenna array 64, e.g., focussing of radiated power from the array 64 to selected points in the target object. The signals picked up by each antenna 63 are transmitted back on the line 61 to the directional coupler 60. The directional couplers provide the received signals on lines 65 to low noise amplifiers 66, the outputs of which are provided on lines 68 to a receiver 70. The receiver 70 also receives the clock pulses from the clock 53 on a line 71 to allow the receiver 70 to time the received signals with respect to the transmitted signals. The receiver 70 detects the microwave signal on a line 68 and converts the received signal to digital waveform data which is processed by a digital signal processor or a computer 72 in accordance with the invention. The image data from the computer 72 or digital signal processor may be displayed, e.g., on a video display terminal 73, or provided to a storage device 74, e.g., CD ROM, magnetic disk, tape, etc. for long-term storage, or transmitted for other purposes.

Treatment for early-stage breast cancer typically involves a lumpectomy or partial mastectomy to remove the carcinoma and its margins, followed by radiation therapy to destroy any remaining cancer cells. For larger tumors, pre-operative chemotherapy may be used to shrink the tumor to conserve a larger portion of the breast. It is well known that the effect of radiation therapy and chemotherapy can be enhanced using microwave hyperthermia, that is, elevating the temperature of the cancerous tissue through microwave energy absorption. The persisting challenge in microwave hyperthermia, however, is to preferentially heat the cancerous tissue without harming superficial and surrounding healthy breast tissues. Sophisticated adaptive focusing algorithms have been developed for use in phased-array hyperthermia treatment, but they require the use of invasive feedback probes located within the tumor. MIST technology offers a non-invasive approach for maximizing power deposition within the tumor and minimizing power deposition elsewhere. The microwave backscatter signals obtained during a low-power MIST scan of the breast inherently contain the information needed to tightly focus a transmitted high-power microwave pulse at the site of a tumor. In this manner, space-time microwave application utilizing the system of FIG. 2, configured to focus the microwave radiation at the position of the detected tumor, can provide hyperthermia treatment to destroy small early-stage cancerous tumors without harming healthy tissue, thereby potentially eliminating the need for breast surgery and conventional radiation to the breast along with the accompanying side effects.

Figure 3:
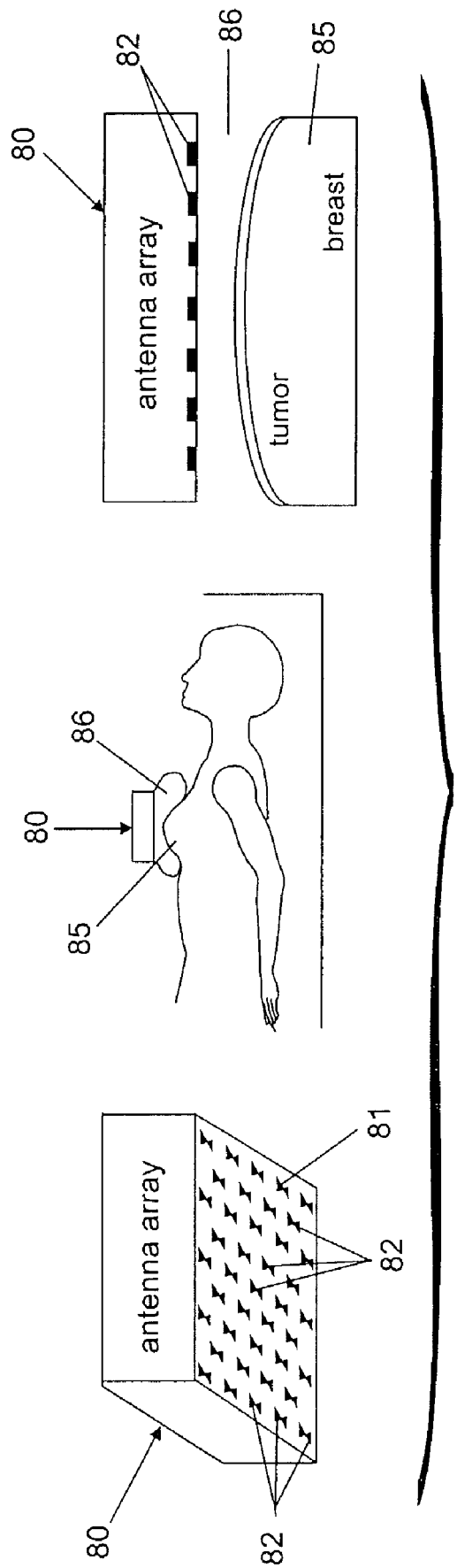
FIG. 3 is an illustrative view of an antenna array and its utilization in the microwave imaging system of the invention.

With reference to FIG. 3, an antenna array device which may be utilized in the microwave imaging system of the invention is shown generally at 80, having a face 81 over which are distributed multiple individual antennas 82 arranged in a two-dimensional array at known locations. The individual antenna elements 82 may have the "bow-tie" shape as shown or other shapes as desired. The array device 80 may be utilized as the antenna array 36 of FIG. 1, with the antenna elements 82 corresponding to the antennas 35, or as the antenna array 64 of FIG. 2, with the antenna elements 82 corresponding to the antennas 63. For purposes of illustration, the antenna array device 80 is also shown in FIG. 3 placed adjacent to the breast 85 or other portion of the body to be imaged, preferably utilizing a matching element 86, such as a liquid filled bag, which conforms to the contour of the breast or other part of the body being imaged to minimize air gaps and unwanted reflections of microwave energy. While the invention is illustrated herein with regard to breast imaging, it is understood that the present invention may be utilized for imaging other parts of the body of an individual.

To achieve the best resolution of the reconstructed image using the space-time focussing approach of the present invention, the radiated microwave pulse is preferably relatively short (e.g., about 100 ps), and thus has a wide band of frequency content, typically from 0 to 20 GHz and with significant energy in the frequency range of 1 GHz to 10 GHz. Thus, it is desirable to utilize antennas that are suitable for transmitting and receiving such short pulses with minimum distortion or elongation. It is desirable that the pulse radiating antenna have a constant sensitivity and a linear phase delay over the bandwidth of the incident electromagnetic pulse in the frequency domain. It is also desirable that the antenna design suppress both feed reflection and antenna ringing, and that the antenna have a smooth transition from the cable impedance at the feed point to the impedance of the immersion medium at the radiating end of the antenna. The return loss, S11, should be low in magnitude as less return loss means more power is transmitted to the antenna. Ideally, the return loss should be constant over the required bandwidth so that the spectrum of the transmitted power is flat and should have a linear phase delay across the frequency band so that the radiated waveform will not be dispersed. Other desirable properties include a well-defined polarization, constant gain, and low side lobes in the radiation pattern. Resistively loaded cylindrical and conical dipole (monopole), and bow-tie antennas can be utilized for radiating temporally short, broad bandwidth pulses. Resistive loading can be utilized to reduce the unwanted reflections that occur along the antenna and the associated distortion of the radiated signal. Spiral antennas and log-periodic antennas have also been designed to achieve wide bandwidth. Spectrum shaping and RF filtering may be needed to enhance the frequency performance of these antennas. Specialized antennas designed for pulse radiation may also be utilized. An example of a suitable antenna that is designed for short pulse radiation is shown and described in U.S. Pat. No. 6,348,898, issued Feb. 19, 2002.

As an example of the present invention, a MIST beamforming system was applied to simulated backscatter data generated from finite-difference time-domain (FDTD) computational electromagnetics simulations of microwave propagation in the breast. The anatomically realistic breast model was derived from a high-resolution 3-D breast MRI (magnetic resonance imaging) obtained during routine patient care at the University of Wisconsin Hospital and Clinics. The face-down images of the pendant breast were digitally rotated, vertically compressed, and laterally expanded to create high-resolution images of the naturally flattened breast of a patient in a supine position. Then, each voxel was assigned the appropriate values of $\in_r$, and $\sigma$. The 2-D model is incorporated into FDTD simulations for a co-linear 17-element monopole antenna array spanning 8 cm along the surface of the breast. Each antenna is excited with an ultrashort differentiated Gaussian pulse (temporal width of 110 ps, bandwidth of 9 GHz) and the backscattered response at the same antenna element is computed. This process is repeated for each element of the array, resulting in 17 received backscattered waveforms. The resulting FDTD-computed backscatter waveforms represent the scattering effects of heterogeneous normal breast tissue (clutter) and the malignant tumor (signal).

The skin response subtraction process estimates the skin component of the signal at each antenna as a filtered combination of the signals at all other antennas. The filter weights are chosen to minimize the residual signal over that portion of the received data dominated by the reflection from an interface with the object being imaged such as the skin-breast interface. The results show that the skin response effect is removed at the expense of energy from the tumor bleeding throughout the image. This occurs because the skin response subtraction algorithm used somewhat distorts the response from the tumor.

The beamformer algorithm utilized first time shifts the 17 received signals to approximately align the returns from a hypothesized scatterer at a candidate location. The time-aligned signals are passed through a bank of finite-impulse response (FIR) filters (one in each antenna channel), summed, and time gated and the power calculated to produce the beamformer output signal. The filters are designed using a least squares technique to present unit gain to scattered signals originating from the candidate location. This technique is described in B. Van Veen, et al., "Beamforming: A Versatile Approach to Spatial Filtering," IEEE ASSP Magazine, Vol. 5, April, 1988, pp. 4-24; B. Van Veen, "Minimum Variance Beamforming," in *Adaptive Radar Detection and Estimation*, Ed. S. Haykin and A. Steinhardt, John Wiley and Sons; New York, Chapter 4, March, 1992, pp. 161-236. Hence, the beamformer output power represents an estimate of the energy scattered by that location. The beamformer is scanned to different locations in the breast by changing the time shifts, filter weights, and time gating. The output power may then be plotted as a function of scan location. Regions of large output power correspond to significant scatterers (e.g., malignant lesions).

A simulation was carried out to determine the scanned MIST output power for a 2-mm-diameter malignant tumor located 3 cm deep. For this study, the average dielectric-properties contrast between malignant and normal breast tissue in the numerical breast phantom is approximately 5:1. The heterogeneity of the normal breast tissue in the numerical breast phantom corresponds to variations in dielectric properties of ±10%, the upper bound on normal breast tissue variability that has been reported. The tumor was clearly detectable, as it stands out from the background clutter by 22 dB. MIST output power for two adjacent 2-mm-diameter tumors separated by 2 cm at a depth of 3 cm, showed two distinct scattering objects are clearly evident at the correct locations, demonstrating the potential resolving power of the present invention. A scenario under the worst-case assumption that the normal-tissue dielectric properties substantially exceed the published upper bound, thereby reducing the dielectric-properties contrast between malignant and normal tissue to less than 2:1, showed that even with significantly reduced contrast, the tumor was still easily detected, as the peak of the tumor response stands 11 dB above the largest background clutter.

The foregoing exemplary beamforming process incorporates frequency dependent propagation effects, but does not incorporate frequency dependent scattering effects. Scattering is frequency dependent due to dispersive dielectric properties and the presence of multiple scattering surfaces. Frequency dependent scattering broadens the received pulse duration, reducing resolution, and shifts the center of received energy in time, which causes scattered signal power to appear at an incorrect location. These errors may be compensated by processing the beamformer output signal from the filters prior to time gating using a parametric signal processing model for frequency dependent scattering effects. For example, autoregressive models may be used to describe the resonant behavior caused by finite tumor size.

Removal of the response from the skin-breast interface is critical for lesion detection, as this response is orders of magnitude larger than the tumor response. This response may be removed at the expense of some distortion of the tumor response. The distortion is known since it is a function of the weights used for skin response removal, allowing processing to be carried out for reducing or eliminating the tumor response distortion.

The skin response removal algorithm estimates the skin response at each antenna. The skin response is a known function of the skin thickness and the dielectric properties of the skin and breast. This fact may be exploited in processes for estimating these properties from the skin response. The average breast dielectric properties may then be used as a calibration step to choose the best beamformer design for each patient.

The methods described above assume only one antenna is transmitting and receiving at any point in time. This process involves sequentially stepping through the array. If an antenna array with multiple receive channels is used as shown in FIG. 2, then a multitude of different transmit-receive strategies are possible. Beamforming and skin response removal algorithms may be utilized in which all antennas receive simultaneously. Transmit strategies may also be utilized that focus the transmitted energy on a given region of the breast. The transmit and receive focus location is then scanned throughout the breast to form the image of scattered power. Such scanning may be utilized to improve resolution and robustness to artifacts, noise, and clutter. The signal parameters used to focus the transmission are the relative transmit time and signal amplitude in each antenna. After a lesion is located, the transmitted energy from the antennas may be focused on the lesion at a higher power level to heat and destroy the lesion.

Methods may be employed for assessing changes in lesion size from images obtained at different points in time. Both the spatial extent of the scattering region as well as the total power returned may increase from one scan to the next if the tumor undergoes angiogenesis and growth. Tracking this growth would be useful in the diagnosis of malignant lesions. Both the spatial extent of the scattering region and the total power returned may decrease if cancerous cells in the lesion are destroyed. Monitoring the decrease in lesion size would aid in assessing the effect of radiation therapy, chemotherapy, and/or thermotherapy. Use of absolute estimated tumor power is problematic due to expected variation from one measurement to the next. However, the peak tumor-to-clutter ratio should be robust to measurement variations and provide a reliable metric for assessing relative tumor size. Frequency dependent scattering effects will also vary with tumor size and provide another means for assessing changes over time.

An exemplary MIST sensor in the imaging system of the invention may include a microwave vector reflectometer (the pulse generator 21, 51 and receiver 42, 70, and may include the associated amplifiers and directional couplers) and a low-reverberation ultrawideband transmitting/receiving antenna. A low-noise commercial vector network analyzer (VNA) with a time-domain option may be used for the vector reflectometer. The dynamic range of a VNA of this type is sufficient to detect small malignant tumors up to depths of 5.0 cm in the breast.

The MIST strategy for detection is to identify the presence and location of strong scatterers in the breast, rather than to attempt to reconstruct the dielectric-properties profile of the breast interior. As a result, the MIST approach overcomes the fundamental computational limitations and related vulnerabilities to noise of conventional narrowband microwave tomography. The use of spatial and temporal focusing in MIST significantly enhances the response from malignant lesions while minimizing clutter signals, thereby overcoming challenges presented by breast heterogeneity. Space-time focusing achieves super-resolution, enabling the detection of extremely small (<5 mm in diameter) malignant lesions with harmless low-power microwave signals. In contrast to earlier examples of breast imaging using ultrawideband microwave-radar techniques, MIST employs sophisticated and robust frequency-dependent processing of microwave backscatter signals to obtain superior sensitivity for discriminating against artifacts and noise. The innovative system configuration eliminates the need for breast compression and permits the interior breast tissue to be imaged with the patient lying comfortably on her back. This uniquely enables MIST to detect tumors located near the chest wall or in the quadrant near the underarm where an estimated 50% of all breast tumors occur.

Reflection artifact removal (such as skin response removal), beam forming, and frequency-dependent scattering processes in accordance with the invention are discussed in further detail below. These processes may be carried out in a separate computer (e.g., the computer 44 of FIG. 1 or 72 of FIG. 2), or in a digital signal processor of the receiver (e.g., the receiver 42 of FIG. 1 or the receiver 70 of FIG. 2), both of which will be referred to herein as a computer, that is programmed to carry out the processing on the digitized waveform signal data for each antenna that is provided by the receiver.

The following describes the artifact removal and beamforming design method in mathematical expressions which are implemented in the computer and/or digital signal processors of the systems of FIGS. 1 and 2. Lower and upper case boldface Roman type is used to denote vector and matrix quantities, respectively. Superscript * represents the complex conjugate and superscripts T, H, and −1 represent the matrix transpose, complex conjugate transpose, and inverse, respectively.

Reflection Artifact Subtraction

A reflection artifact removal process is preferably carried out on the data received from the antennas to remove large reflection artifacts, such as the energy reflected from the ends of the antenna and feed and from the skin-breast interface. These reflections are typically orders of magnitude greater than the received backscatter signal. This reflection artifact removal or subtraction process will be described below for the example of removal of the skin-breast interface response. The skin response removal process forms an estimate of the response associated with the skin-breast interface and subtracts it from the recorded data. The response from the skin-breast interface is a function of the skin thickness, the dielectric properties of the skin, and the dielectric properties of the breast. Thus, the response from the skin-breast interface can be used to estimate these parameters. This is accomplished in general by expressing the response from the skin-breast interface as a parametric function of the unknown parameters and then choosing the unknown parameters to minimize the mean-squared error between the measured skin-breast response (the data) and the parametric function. That is, we choose the skin thickness and dielectric properties of the skin and breast so that the predicted response most closely approximates the actual measured response.

Figure 4:
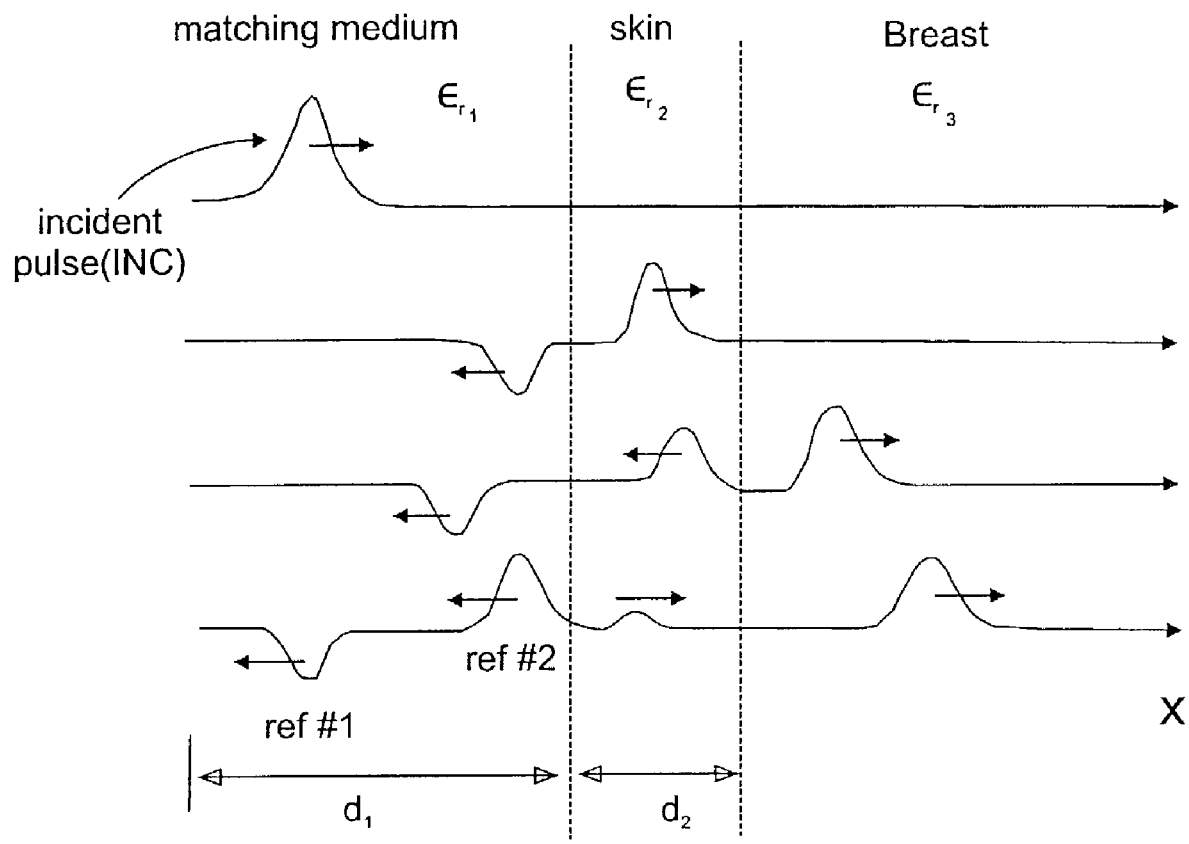
FIG. 4 are spatial waveforms illustrating pulses reflected from the skin.
Figure 5:
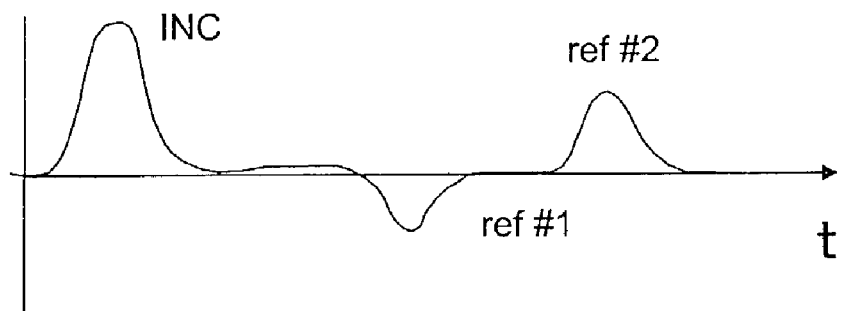
FIG. 5 is an illustrative temporal waveform at an antenna showing reflected pulses from the skin interfaces.

To illustrate this, consider the simple case in which the dielectric properties are assumed to be frequency independent, the skin-breast interface is assumed planar, and the transmitted signal propagates as a plane wave. To further simplify the illustration, we assume lossless propagation where the permittivity $\in_{r1}$ of the matching medium (e.g., the liquid matching medium 86 of FIG. 3) is known and the permittivity of the skin $\in_{r2}$ and the permittivity of the breast tissue $\in_{r3}$ are unknown. FIG. 4 illustrates the incident and reflected pulses at the skin/breast interface at four points in time, assuming an ultrashort microwave pulse. FIG. 5 illustrates the observed temporal waveform at the antenna which includes the pulse reflected from the matching medium/skin interface (Ref #1) and the pulse reflected from the skin/breast tissue interface (Ref #2) (in practice, these reflected pulses will overlap). Let $v_{inc}(t)=v(t)$ represent the incident pulse. Then the first reflected pulse (Ref. #1) may be represented as $$v_{ref1}(t) = \Gamma_{12} v\left(t - \frac{2d_1\sqrt{\varepsilon_{r1}}}{c}\right)$$

and the second reflected pulse (Ref #2) may be represented as $$v_{ref2}(t) = T_{12}\Gamma_{23}T_{21} v\left(t - \frac{2d_1\sqrt{\varepsilon_{r1}}}{c} - \frac{2d_2\sqrt{\varepsilon_{r2}}}{c}\right)$$

where $$\Gamma_{12} = \frac{\sqrt{\varepsilon_{r1}} - \sqrt{\varepsilon_{r2}}}{\sqrt{\varepsilon_{r1}} + \sqrt{\varepsilon_{r2}}}$$

$$T_{12} = \frac{2\sqrt{\varepsilon_{r1}}}{\sqrt{\varepsilon_{r1}} + \sqrt{\varepsilon_{r2}}}$$

$$\Gamma_{23} = \frac{\sqrt{\varepsilon_{r2}} - \sqrt{\varepsilon_{r3}}}{\sqrt{\varepsilon_{r2}} + \sqrt{\varepsilon_{r3}}}$$

$$T_{21} = \frac{2\sqrt{\varepsilon_{r2}}}{\sqrt{\varepsilon_{r1}} + \sqrt{\varepsilon_{r2}}}$$

and c is the free space propagation velocity.

Hence, the observed waveform due to the incident pulse, the reflected pulse #1 and the reflected pulse #2 has the form $r(t)=v(t)+a_1 v(t-t_1)+a_2 v(t-t_1-t_2)$ where $v(t)$ is known.

We may correlate $v(t)$ with $r(t)$ and estimate $t_1$, $a_1$ from the second peak (in time) and $a_2$, $t_2$ from the third peak using standard time-delay/amplitude estimation techniques.

Given $t_1$, $a_1$, $t_2$, $a_2$ we may solve for $d_1$, $d_2$, $\sqrt{\varepsilon_{r2}}$, $\sqrt{\varepsilon_{r3}}$ as follows:

$$d_1 = \frac{ct_1}{2\sqrt{\varepsilon_{r1}}} \quad \sqrt{\varepsilon_{r2}} = \frac{(1-a_1)}{(1+a_1)}\sqrt{\varepsilon_{r1}}$$

$$d_2 = \frac{ct_2}{2\sqrt{\varepsilon_{r2}}} = \frac{(1+a)ct_2}{(1-a_1)2\sqrt{\varepsilon_{r1}}}$$

$$\sqrt{\varepsilon_{r3}} = \frac{\alpha - a_2 \partial}{a_2 \delta + \beta}$$

where $$\alpha=4\sqrt{\varepsilon_{r1}}(\sqrt{\varepsilon_{r2}})^2 \beta=4\sqrt{\varepsilon_{r1}}\sqrt{\varepsilon_{r2}}$$

$$\delta=(\sqrt{\varepsilon_{r1}}+\sqrt{\varepsilon_{r2}})^2 \partial=\sqrt{\varepsilon_{r2}}\delta$$

There are many different techniques for estimating time delays and amplitudes of a known waveform that are well known. The same general methods for determining the dielectric properties may be applied to more realistic models of the skin-breast interface. The following discusses the preferred solution of the skin response removal problem in further detail.

Consider an array of N antennas and denote the received signal at the $i^{th}$ antenna as $b_i(t)$. Each received signal is converted to a sampled waveform, $b_i[n]$, by an A/D converter in the receiver operating at a sampling frequency $f_s$. The received signal contains contributions from the skin-breast interface, clutter due to heterogeneity in the breast, the backscatter from lesions, and noise. The response from the skin-breast interface is orders of magnitude larger than the response from all other contributions and thus must be removed prior to performing tumor detection.

Figure 6:
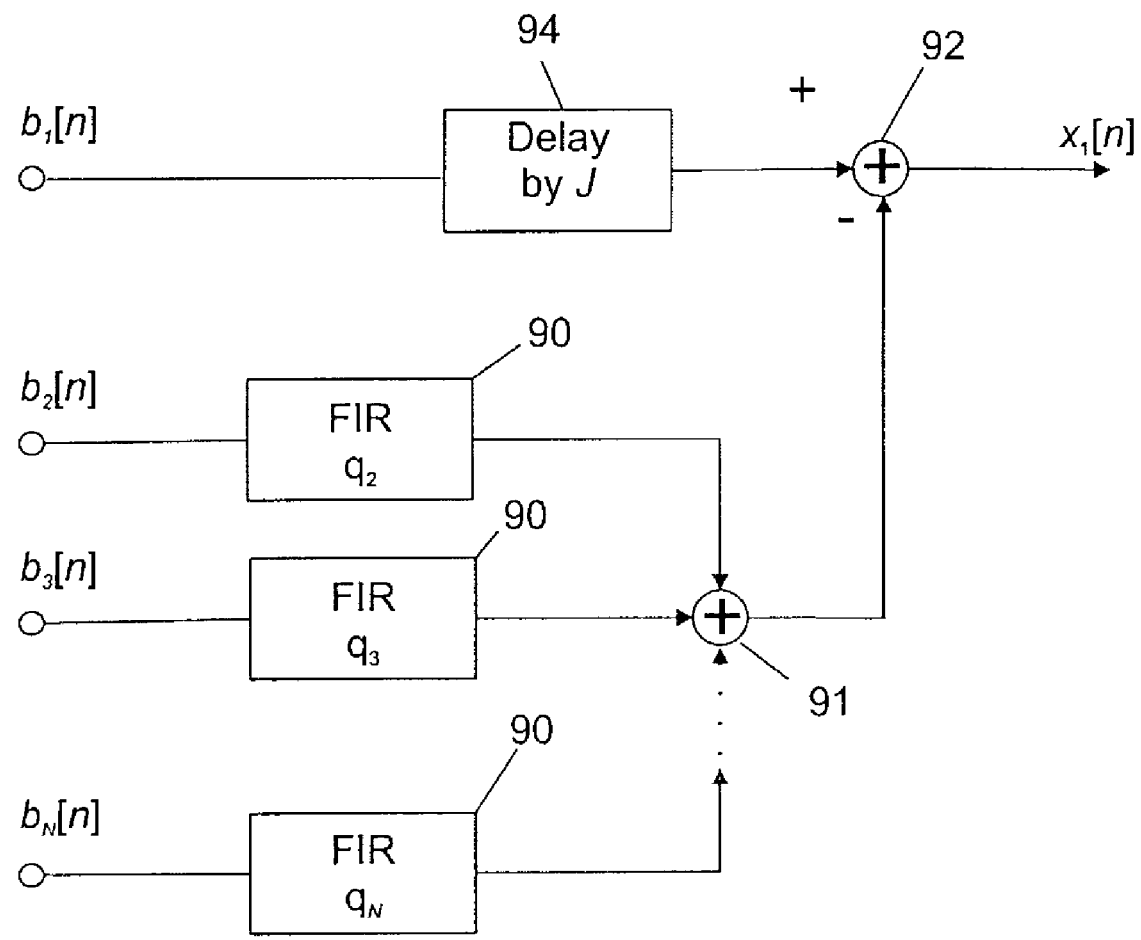
FIG. 6 is a block diagram illustrating the process of artifact removal from a backscattered signal at the first antenna (antenna 1).

The skin artifacts in each of the N channels are similar but not identical due to local variations in skin thickness and breast heterogeneity. If the skin artifact for all channels were identical, one approach to remove it would be to subtract the average of the skin artifact across the N channels from each channel. In order to compensate for channel to channel variation in the skin artifact, the skin artifact at each antenna may be estimated as a filtered combination of the signal at all other antennas, as shown in FIG. 6. The signals from each of the other antennas are provided to FIR filters 90, the outputs of which are summed at 91 and subtracted at 92 from the signal from the particular antenna after a delay 94. The filter weights of the FIR filters 90 are chosen to minimize the residual signal mean-squared error over that portion of the received data dominated by the reflection from the skin-breast interface. Without loss of generality, suppose that the skin artifact is to be removed from the first antenna. Define the $(2J+1)\times 1$ vector of time samples in the $i^{th}$ antenna channel as $$b_i[n]=[b_i[n-J], \ldots, b_i[n], \ldots, b_i[n+J]]^T, 2 \leq i \leq N \quad (1)$$

and let $b_{2N}[n]=[b_2^T[n], \ldots, b_N^T[n]]^T$ be the concatenation of data in channels 2 through N. Similarly, let $q_i$ be the $(2J+1)\times 1$ vector of FIR filter coefficients in the $i^{th}$ channel and $q=[q_2^T, \ldots, q_N^T]^T$ be the concatenation of FIR (finite impulse response) filter coefficients from channels 2 through N. The optimal filter weight vector is chosen to satisfy $$q = \arg\min_q \sum_{n=n_0}^{n_0+m-1} |b_1[n] - q^T b_{2N}[n]|^2 \quad (2)$$

where $n_0$ is the time that approximates when the skin artifact begins and m is the duration of the received signal that is dominated by the skin artifact. The solution to this minimization problem is given by $$q=R^{-1}p \quad (3)$$

$$R = \frac{1}{M} \sum_{n=n_0}^{n_0+m-1} b_{2N}[n]b_{2N}^T[n] \quad (4)$$

$$p = \frac{1}{M} \sum_{n=n_0}^{n_0+m-1} b_{2N}[n]b_1[n] \quad (5)$$

The fact that there is a high degree of correlation among the skin artifacts in the N channels results in the sample covariance matrix R being ill-conditioned. If R is ill-conditioned, then the matrix inversion in equation (3) can result in a solution for q that has very large norm and thus amplifies noise. In order to prevent this, we replace R with the low rank approximation $$R_p = \sum_{i=1}^{p} \lambda_i u_i u_i^T \quad (6)$$

where $\lambda_i, 1 \leq i \leq p$, are the p significant eigenvalues and $u_i, 1 \leq i \leq p$, are the corresponding eigenvectors. The filter weight vector is determined by replacing $R^{-1}$ in equation (3) with $$R_p^{-1} = \sum_{i=1}^{p} \frac{1}{\lambda_i} u_i u_i^T \quad (7)$$

The skin artifact is then removed from the entire data record of the first channel to create artifact free data $x_1[n]$ given by $$x_1[n]=b_1[n]-q^T b_{2N}[n] \quad (8)$$

This algorithm introduces a small level of distortion in the backscattered lesion signal because the backscattered lesion signals from the other N−1 channels are added back in to the first channel. This is explicitly shown by decomposing $b_1[n]$ and $b_{2N}[n]$, into a skin artifact $s_1[n]$ and $s_{2N}[n]$ and residuals $d_1[n]$ and $d_{2N}[n]$, respectively. The residual signals contain the backscattered response from the lesion. The values $n_0$ and m are chosen so that q is determined from a portion of the data in which the residuals are negligible and, thus, $$s_1[n]-q^T s_{2N}[n] \approx 0 \quad (9)$$

However, decomposing $b_1[n]$ and $b_{2N}[n]$ in equation (8) gives $$x_1[n] = s_1[n] - q^T s_{2N}[n] + d_1[n] - q^T d_{2N}[n] \quad (10)$$

$$\approx d_1[n] - q^T d_{2N}[n] \quad (11)$$

Figure 11:
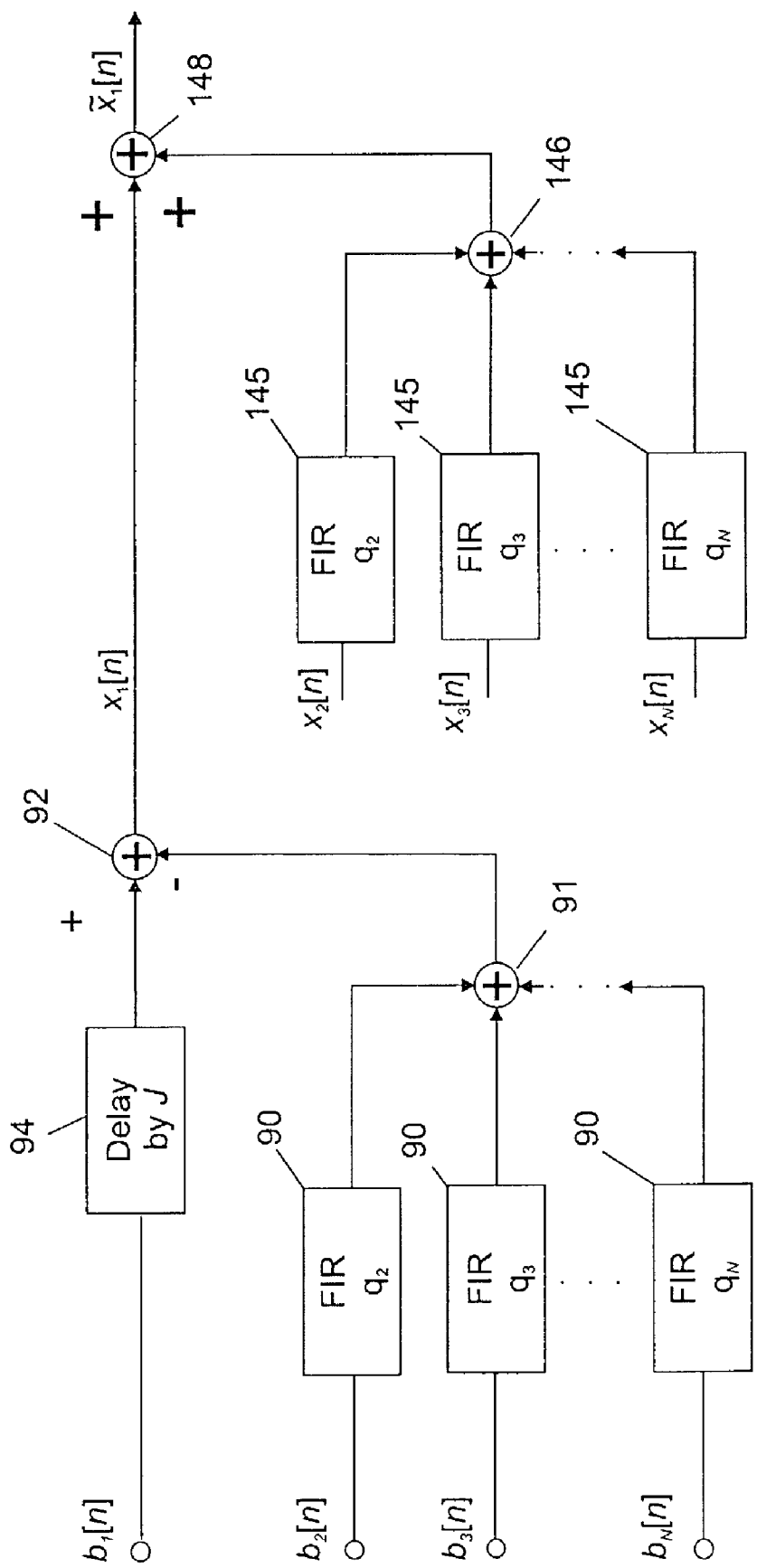
FIG. 11 is a block diagram as shown in FIG. 6 with an addition of a component to reduce distortions from the skin response removal process.

Thus, the residual signal is distorted by $q^T d_{2N}[n]$. This term is generally small because q tends to "average" across channels and the lesion responses in $d_{2N}[n]$ do not add in phase because they are not aligned in time. A simple method for reducing the distortion is to add a filtered version of the residual to obtain $$\tilde{x}_1[n] = x_1[n] + q^T x_{2N}[n] \quad (12)$$

where $$x_{2N}[n] = [x_2[n-J], \ldots, x_2[n+J], \ldots, x_N[n-J], \ldots, x_N[n+J]]^T \quad (13)$$

is the vector containing the data from the other N−1 channels after the skin artifact has been removed from each of them. This addition of a filtered form of the residual is illustrated in FIG. 11 which includes FIR filters 145 to provide filtered signals that are summed at 146 to produce a signal added at 148 to the corrected data signal $x_1[n]$ to provide an improved corrected signal data $\tilde{x}_1[n]$.

Figure 8:
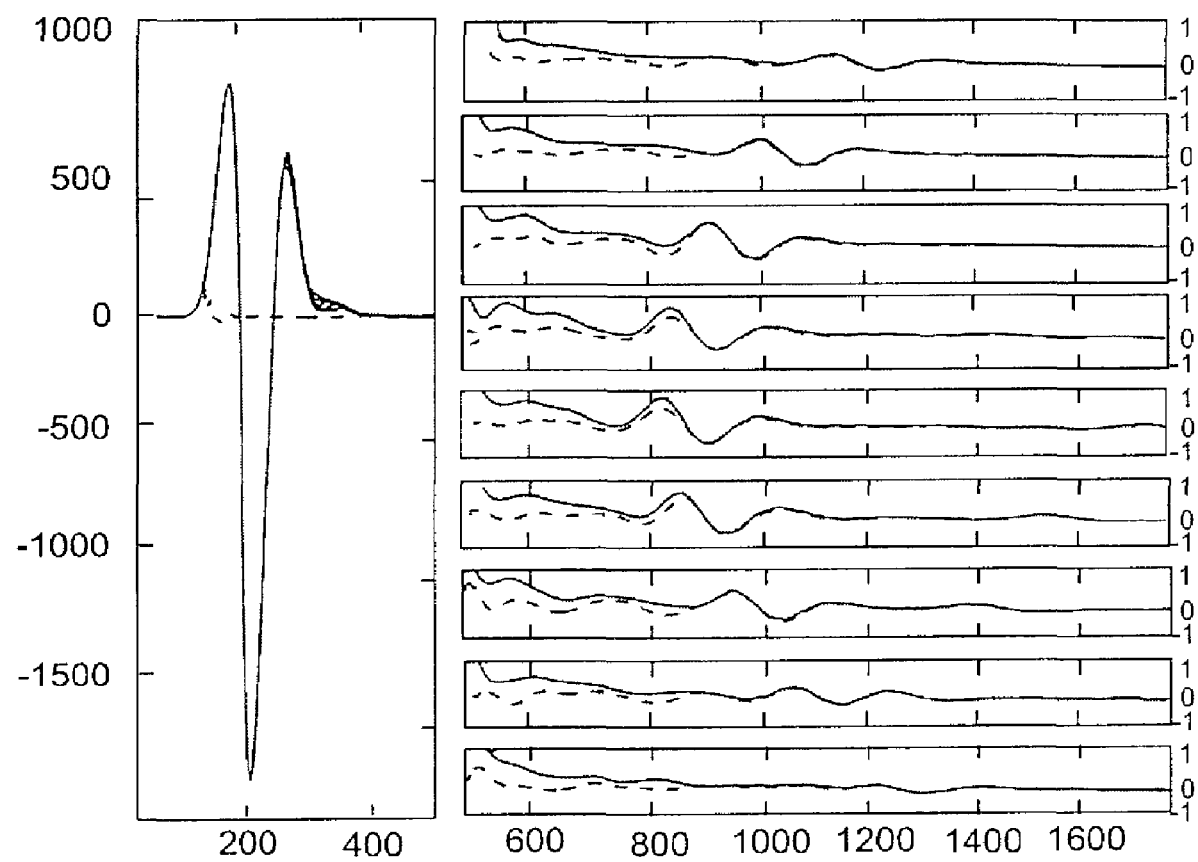
FIG. 8 are time waveforms showing skin artifact removal, with the solid curve showing the original waveforms and the dashed curves corresponding to the waveforms after application of the skin artifact removal algorithm.

FIG. 8 are example waveforms showing the effect of the skin response subtraction process, with the solid lines indicating the original waveforms and the dashed lines indicating the waveforms after skin artifact removal.

The artifact subtraction process can be applied only in the time domain. Thus, if frequency scanning is carried out using multiple discrete frequencies of the signals applied to the antennas, the received signal data must first be converted to the time domain (using an inverse FFT) prior to applying the artifact subtraction process.

The artifact removal process requires that all of the artifacts occur at the same relative times in the different channels. If the antennas are located at varying distances from the skin, the skin response will occur at different times. Thus, to apply the algorithm in general, the waveforms must first be time shifted so artifacts in all channels occur simultaneously. Aligning the artifacts in time is trivial because by nature the artifact is huge and it is easy to see when it starts.

The antenna reflection response will not vary in time in the different channels (assuming nearly identical antennas), so time alignment is not needed for removing it. The algorithm can simultaneously remove antenna artifact and skin reflection artifact, provided they are both time aligned in the waveforms. While this is true if the array is not the surface of the skin, it is not generally true if the distances to the skin differ for different antennas. In this case, one can apply the algorithm twice: first, to remove the antenna response, followed by time alignment of the residual skin response, and second remove the skin response.

There is one limitation with applying it twice, and that has to do with the other requirement of the algorithm, which requires the artifact to be the only contribution to the signal over a time interval that spans at least part of the artifact duration. Hence, if the antennas are varying distances from the skin, but in some channels the skin response completely overlaps (in time) the antenna response, it may not perform adequately.

Space-Time Beamforming

Figure 7:
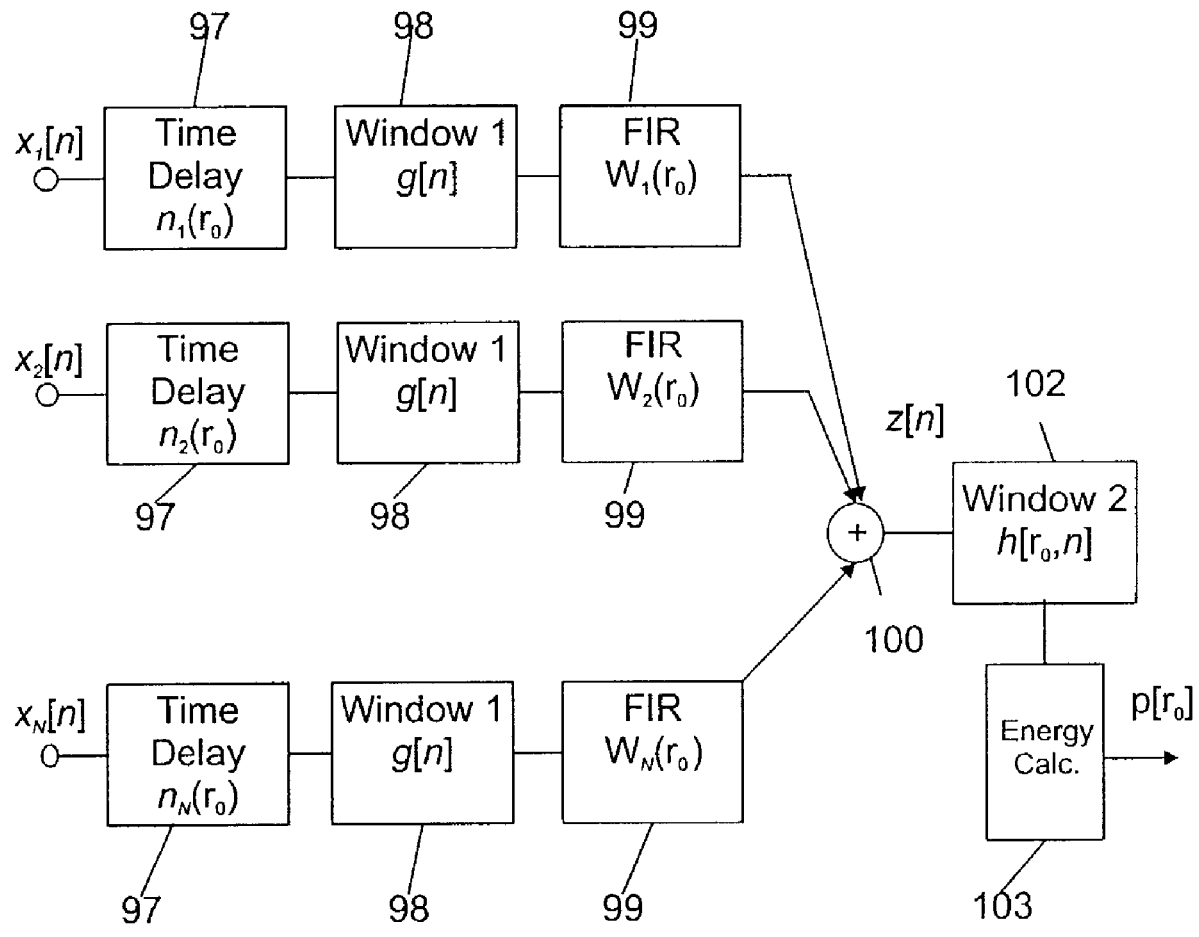
FIG. 7 is a block diagram of a space-time beamformer for a location $r_0$ utilizing time-domain processing.

The image of backscattered power as a function of a location r is obtained by scanning each location with a different space-time beamformer. The beamformer for scan location r forms a weighted combination of time-delayed versions of a signal as shown in FIG. 7. Each of the signals $x_1[n]$ from the antennas after subtraction of the skin response is passed through a time delay 97, a first time window 98, and an FIR filter 99. The outputs of the filters 99 are summed at 100. The summed output is passed through a second time window 102 to an energy calculation 103. The calculation of the energy in the signal over a consistent period of time provides a result which is proportional to power in the signal, and will be considered herein as the same as calculation of power. Preferably, the beamformer is designed to pass backscattered signals from the location r with unit gain, while attenuating signals from other locations.

For design purposes, assume that the received signal on the $i^{th}$ channel is only comprised of the response due to a lesion at location r. Let this signal be denoted by $x_i[n]$ having Fourier transform $X_i(\omega)$. Note that the received signal is $$X_i(\omega) = P(\omega) V_i(r, \omega) \quad 1 \leq i \leq N \quad (14)$$

where $P(\omega)$ is the Fourier transform of the transmitted pulse $p(t)$ and $V_i(r, \omega)$ is the frequency response of the electromagnetic model representing frequency dependent propagation and scattering effects. The $i^{th}$ sampled waveform is then delayed by an integer number of samples $n_i(r) = n_a - \tau_i(r)$, resulting in the waveforms in each channel being approximately aligned in time. The average time $\tau_i(r)$ denotes the roundtrip propagation delay for location r in the $i^{th}$ channel, computed by dividing the roundtrip path length by the average speed of propagation and rounding to the nearest sample, and $n_a$ is the reference time to which all received signals are aligned. We choose $n_a$ as the worst case delay over all channels and locations, that is, $$n_a \geq \text{round}\left(\max_{i,r} \tau_i(r)\right) \quad (15)$$

The time aligned signals are windowed before the filtering stage, to remove interference and clutter prior to $n_a$ that could contribute to the FIR filter outputs, using the window function $$g[n] = \begin{cases} 1 & \text{if } n \geq n_a \\ 0 & \text{otherwise} \end{cases} \quad (16)$$

The FIR filter in the $i^{th}$ channel has coefficients represented by the L×1 vector $w_i$. The FIR filters equalize path length dependent dispersion and attenuation, interpolate any fractional time delays after time shifting, and bandpass filter the signal. The frequency response of each filter can be written as $$W_i(\omega) = \sum_{l=0}^{L-1} w_{il} e^{-j\omega lT_s} = w_i^T d(\omega) \quad (17)$$

where $T_s=1/f_s$ is the sampling interval and $d(\omega)=[1,e^{-j\omega T_s},\ldots,e^{-j\omega(L-1)T_s}]^T$. In order to pass signals from a location $r_0$ with unit gain and a linear phase shift, we require $$\sum_{i=1}^{N} V_i(r_0,\omega)e^{-j\omega n_i(r_0)}W_i(\omega) = \quad (18)$$

$$\sum_{i=1}^{N} \tilde{V}_i(r_0,\omega)e^{-j\omega \tau_i(r_0)}e^{-j\omega n_i(r_0)}w_i^T d(\omega) \approx e^{-j\omega(T_s(L-1)/2+n_a)}$$

$$i = 1, 2, \ldots, N$$

where $\tilde{V}_i(r_0,\omega)$ is the frequency response of the electromagnetic model after removing the average propagation and $T_s(L-1)/2$ represents the average time delay introduced by the FIR filter. Thus, the design constraints on $w_i$ are $$\sum_{i=1}^{N} \tilde{V}_i(r_0,\omega)w_i^T d(\omega) \approx e^{-j\omega T_s(L-1)/2} \quad (19)$$

If these constraints are satisfied, then the summed output of the FIR filter bank, $z[n]$, has the Fourier transform $$Z(\omega)=P(\omega)e^{-j\omega(T_s(L-1)/2+n_a)} \quad (20)$$

This signal is windowed with $h[r_0,n]$ to eliminate additional clutter, and the power in the windowed signal is obtained by taking the sum of the square of each sample. The following sections discuss how the filter weights are designed and how the window $h[r_0,n]$ is obtained.

FIR Filter Design

Let the $NL \times 1$ filtering vector be $w=[W_1^T,\ldots,W_N^T]^T$. We may rewrite equation (19) as $$W^T d(r_0,\omega) \approx e^{-j\omega T_s(L-1)/2} \quad (21)$$

where the $NL \times 1$ array response vector corresponding to coordinate $r_0$ is $$d(r_0,\omega)=d(\omega)\otimes[\tilde{V}_1(r_0,\omega),\ldots,\tilde{V}_N(r_0,\omega)]^H \quad (22)$$

Here the symbol $\otimes$ denotes the kronecker product and superscript H denotes complex conjugate transpose. The filters are designed using a least squares technique to approximate equation (21) across the band of frequencies $[\omega_l,\omega_u]$ while attenuating signals from other directions. This is accomplished by seeking to approximate equation (21) on a dense grid of M distinct frequencies. To ensure that $w$ is real-valued, we use positive and negative frequency pairs. Define the matrix of array response vectors for M frequencies as $$A=[d(r_0,\omega_1),\ldots,d(r_0,\omega_M)] \quad (23)$$

So, equation (21) is expressed as $$W^T A \approx f_d \quad (24)$$

where $$f_d=[e^{-j\omega_1 T_s(L-1)/2},\ldots,e^{-j\omega_M T_s(L-1)/2}]^T \quad (25)$$

Thus, the least squares design problem can be written as $$\min_{w}\|A^H w - f_d\|_2^2 \quad (26)$$

The minimum-norm solution to this problem is $$W=(AA^H)^{-1}Af_d \quad (27)$$

The solution may have a very large norm if A is ill-conditioned. A large norm can cause the gain at locations other than $r_0$ to become large and also amplify noise. In order to control these effects, we choose w to solve the penalized least squares problem $$\min_{w}\|A^H w - f_d\|_2^2 + \lambda\|w\|_2^2 \quad (28)$$

where $\lambda$ is a constant chosen to trade the norm of w against the approximation error. The solution is $$W=(AA^H+\lambda I_{NL\times NL})^{-1}Af_d \quad (29)$$

Window Design

The purpose of the second window 102 having the window function $h[r_0, n]$ is to reduce residual interference and clutter in the signal $z[n]$. In the design process, the $z[n]$ is obtained by assuming the received signals are due to a point source at $r_0$ and by passing these signals through the designed space-time beamformer. The leading edge of the window is placed at the start of the beamformer output due to a point source. The response from finite size lesions have longer duration than that of the point source due to frequency dependent scattering effects. Hence, in order to capture the majority of the backscattered energy from the lesions, the window length should be chosen based on the approximate duration of actual expected responses from finite size lesions. If the window is too long, then the background clutter level increases and resolution decreases. As an example, the length of the window may typically be selected for tumor sizes having a diameter in the range of 2 mm to 8 mm.

Frequency Dependent Scattering

A lesion may introduce frequency-dependent scattering due to frequency dependence in its dielectric properties (and those of the surrounding medium). There is also the effect of energy resonating in the "cavity" represented by the lesion (reverberant scattering within the lesion). This effect will depend on the size of the lesion and its morphology.

We expect frequency dependence in the scattered signal to be of use in monitoring lesion growth as well as diagnosis (e.g., differentiating malignant from benign based on morphology).

The model is $$X_i(\omega)=P(\omega)V_i(r,\omega) \quad 1 \leq i \leq N \quad (30)$$

This assumes a "point scatterer" or frequency-independent scatterer since $P(\omega)$ is the Fourier transform of the transmitted pulse and $V_i(r, \omega)$ is the propagation path frequency response.

A first-order frequency-dependent scattering model is $$X_i(\omega)=P(\omega)A(\omega)V_i(r_0,\omega) \quad 1 \leq i \leq N \quad (31)$$

This model assumes the lesion modifies the spectrum of the incoming pulse with $A(\omega)$. This is a first-order model because it ignores possible dependence on i.

The beamformer output for location $r_0$ (prior to time gating) has the frequency response $$Z(r_0,\omega)=P(\omega)A(r_0,\omega)T(r_0,\omega) \quad (32)$$

where $$T(r_0, \omega) = \sum_{i=1}^{N} \tilde{V}_i(r_0, \omega) w_i^T d(\omega) e^{-j\omega n_a} \quad (33)$$

is the frequency response due to propagation and beamforming, and is known given $r_0$, $W_i$, $n_a$, and the average dielectric properties. $P(\omega)$ is also assumed known (or can be measured). The problem is to identify $A(r_0,\omega)$. This is a classic system identification problem We have $$A(r_0, \omega) = \frac{Z(r_0, \omega)}{P(\omega)T(r_0, \omega)}$$

The division in the frequency domain shown here is for conceptual purposes. In practice, this approach is sensitive to noise and small values of $P(\omega)$ $T(r_0, \omega)$ and other system identification methods may be used.

It is in general preferable to use a parametric model for $A(r_0, \omega)$ to minimize modeling of extraneous clutter at the output of the beamformer. Standard models that may be used to this end include autoregressive (all pole), moving-average (all zero), and autoregressive-moving average (pole-zero). Methods for determining model parameters from system input and output data are well known.

To illustrate, consider using an all-pole (AR) model. This is well suited to describing resonance effects. We shall formulate this problem in the time domain. Let $P_T(n)$ be the beamformer output calculated assuming a point scatterer, and $z(r_0, n)$ be the actual output. We drop $r_0$ from now on.

Here $a_i$ represents the AR coefficients. The model states $$a_0 z(n)+a_1 z(n-1)+a_2 z(n-2)+\ldots+a_p z(n-p)=p_T(n) \quad (34)$$

The presence of noise and modeling error will cause this to be an approximation. One method for choosing the $a_i$'s is to minimize the approximation error.

Given $z(n), p_T(n), n=0,1,\ldots Q$ $(Q>P)$ we may write this as $$\begin{bmatrix} z(p) & z(p-1) & \ldots & z(0) \\ z(p+1) & z(p) & \ldots & z(1) \\ \vdots & & & \vdots \\ z(Q) & z(Q-1) & \ldots & z(Q-P) \end{bmatrix} \begin{bmatrix} a_0 \\ a_1 \\ \vdots \\ a_p \end{bmatrix} \approx \begin{bmatrix} p_T(p) \\ p_T(p+1) \\ \vdots \\ p_T(Q) \end{bmatrix} \quad (35)$$

One means for identifying a is to solve this problem in the least-squares sense. Many other methods can also be formulated, as is well known.

The frequency response is expressed in terms of the $a_i$'s as $$A(\omega) = \frac{1}{a_0 + a_1 e^{-j\omega} + a_2 e^{-j2\omega} + \ldots a_p e^{-j\omega p}} \quad (36)$$

Figure 9:
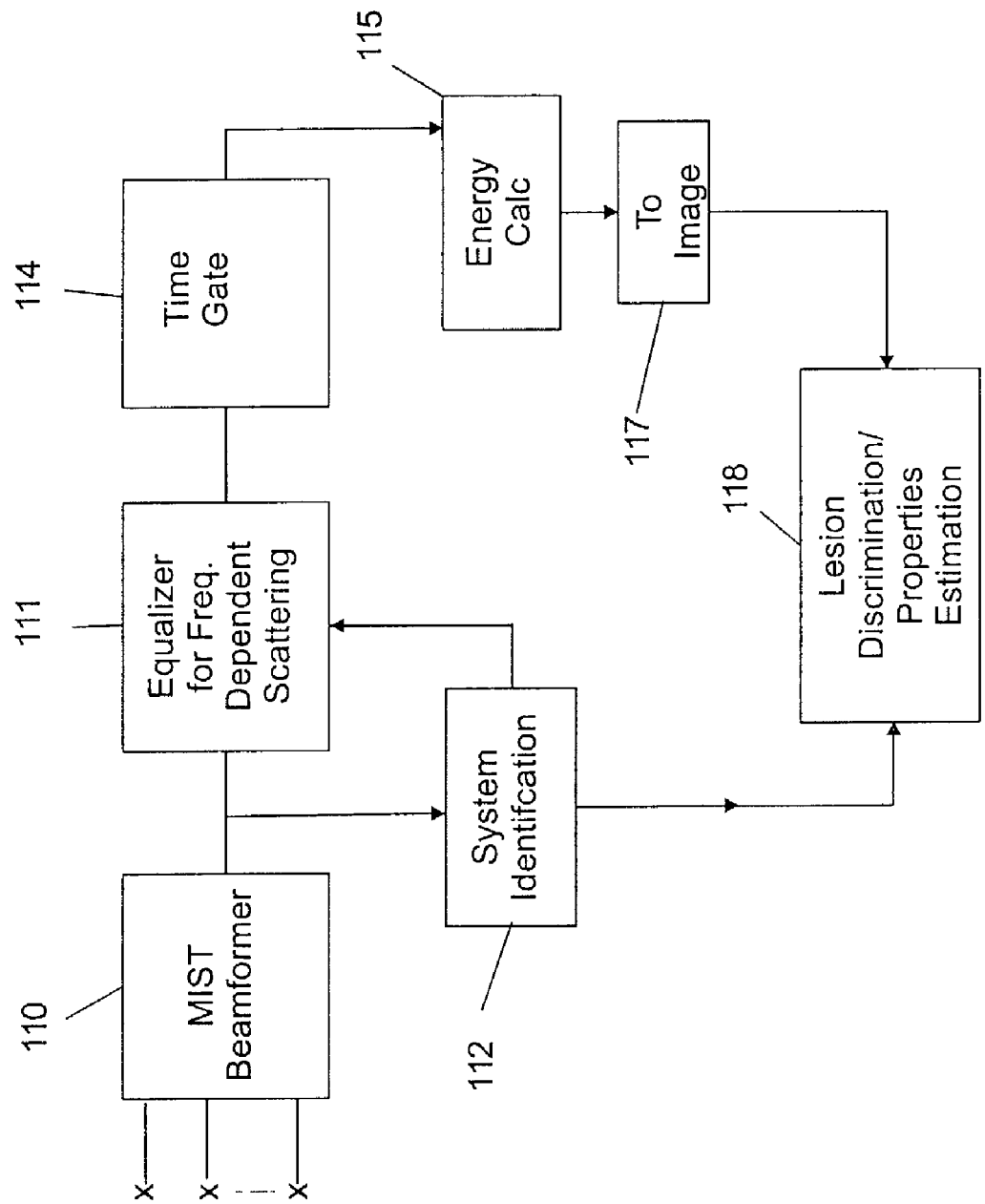
FIG. 9 is a block diagram illustrating a preferred process for accommodating frequency-dependent scattering.

Given a model for $A(\omega)$, one can potentially discriminate between classes of lesions or lesion size. It is also helpful to "equalize" the effects of the frequency-dependent scattering prior to time gating the beamformer output and forming an image. This equalization can reduce the sensitivity of the time-gate duration to tumor size. The duration of the back-scattered signal varies due to frequency dependent scattering and thus if these effects are not equalized, the time-gate duration must be chosen long enough to capture sufficient energy from lesions with long duration backscatter. This reduces resolution for lesions with short duration backscatter. Thus, a preferred method for accommodating frequency-dependent scattering is shown in FIG. 9. As illustrated therein, the output of the beamformer 110 is provided to an equalizer 111 and to a system identifier 112 (which also provides control signals to the equalizer 111). The output of the equalizer 111 is provided through a time gate 114 to a power calculator 115 which provides its results to an image generator 117. Information from the image and from system identification is provided to a lesion discrimination/properties estimator 118.

Various techniques for equalizing signals are well known in the communications and signal processing literature and may be utilized. Note that the equalizer should not remove the average "gain" of the frequency dependent scattering since this factor is needed to get a correct relative estimate of backscattered power.

Beamformer Design in the Frequency Domain

A frequency-domain design approach may also be utilized for microwave imaging via space-time beamforming. The frequency domain design MIST beamformer spatially focuses the backscatter waveforms, compensates for frequency-dependent propagation effects, and discriminates against artifacts and noise. This is accomplished by time-aligning the backscatter, followed by frequency dependent filtering in each antenna channel. The filter frequency responses preferably solve a penalized least squares problem designed to pass signals from a candidate scattering location in the breast with unit gain, subject to soft constraints on the norms of the filters for each channel. The MIST beamforming can produce a 3-D image of the relative backscatter energy, where each pixel of the image represents the energy of the backscatter originating from the corresponding location in the breast. Image locations with high energy implicate the presence of malignant tissue. The frequency-domain MIST design can provide a less computationally intense solution. Given M channels and L filter coefficients per channel, time-domain MIST beamformer design requires inversion of an ML×ML matrix for each pixel in the design stage. The frequency-domain design circumvents matrix inversions altogether at the cost of selecting multiple penalty weights rather than a single one.

The MIST beamformer for either the time- or frequency-domain designed filters may be implemented in the frequency domain using a series of single frequency measurements to synthesize a broadband input. Assuming M channels and N DFT (discrete Fourier transform) frequencies, the imaging procedure involves an N-point FFT (fast Fourier transform) on the data in each of the M channels, one IFFT (inverse fast Fourier transform) plus the matrix multiplication of two N×M matrices. Thus, the number of computations for each image pixel is on the order of $(M+1)N \log N+2MN^2$.

For simplicity we consider the monostatic case which is a single-transmit, single-receive configuration. Extensions to the single-transmit, multiple-receive configuration are straightforward. In the monostatic case each antenna, in turn, transmits a pulse into the breast and collects the resulting backscatter before the next antenna repeats the sequence. The collected signals are converted to sampled waveforms containing contributions from the skin-breast interface, clutter due to heterogeneity in the breast, backscatter from possible lesions, and noise. Since the response from the skin-breast interface is much larger than the response from all other contributions, it must be removed prior to performing tumor detection. We accomplish this with the skin-breast artifact removal algorithm presented above which estimates the skin-breast artifact in each channel as a filtered combination of the signals in all other channels. The filter weights are chosen to minimize the residual signal mean-squared error over that portion of the received data dominated by the reflection from the skin-breast interface. This algorithm is shown to effectively eliminate the skin-breast artifact while introducing only a very small level of distortion in the signal backscattered from the lesion.

Figure 10:
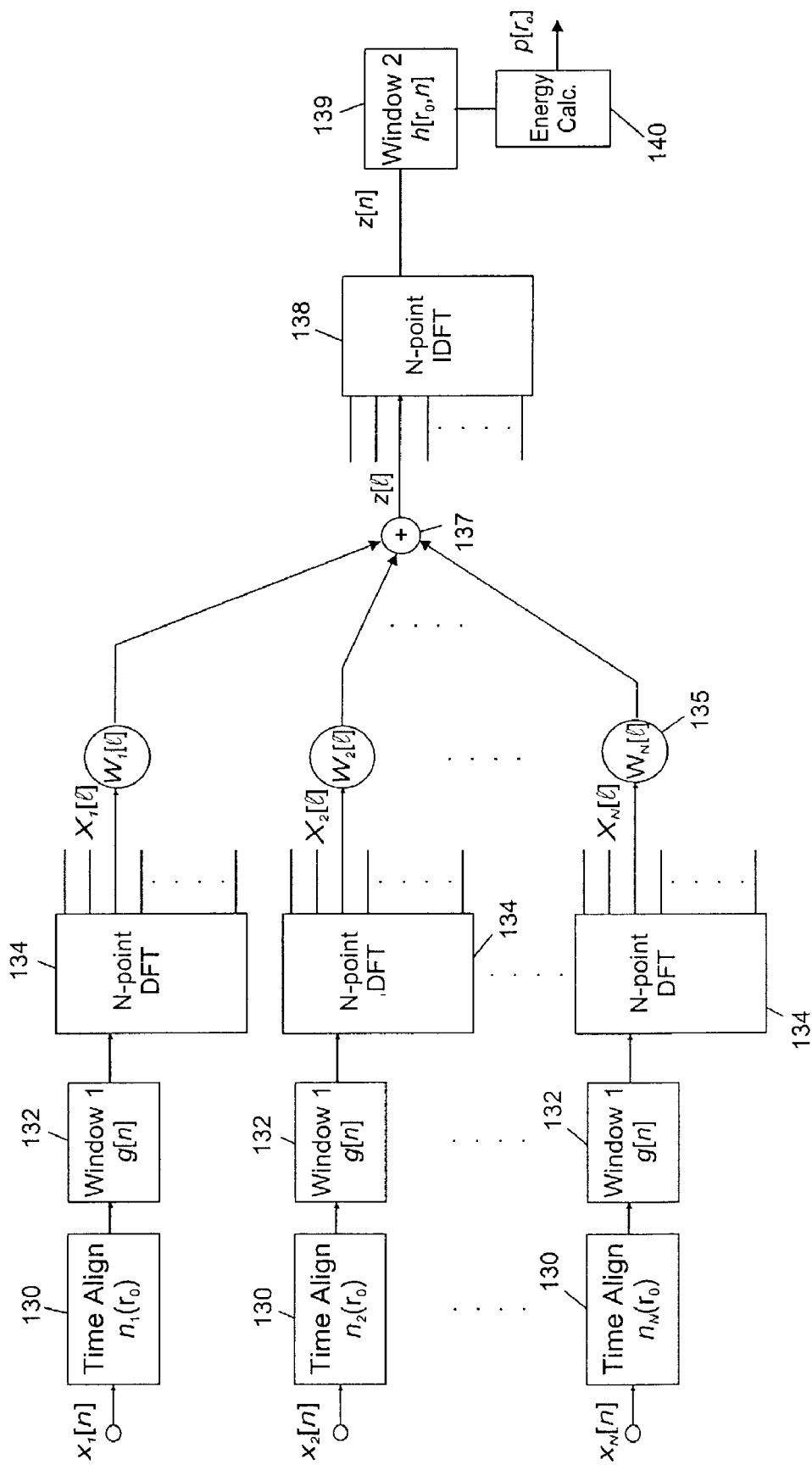
FIG. 10 is a block diagram of another space-time beamformer for a location $r_0$ utilizing frequency domain processing.

The image of backscattered energy as a function of scan location r is obtained by applying a space-time beamformer designed for each scan location to the backscattered signals. FIG. 10 illustrates the post-processing performed on the signals for a specific scan location, $r_0$, following the skin-breast artifact removal. The signals $X_i[n]$ are time aligned with an appropriate time delay 130, windowed at 132, transformed to the frequency domain at 134 and pointwise multiplied by the beamformer coefficients at 135. The sum of these weighted signals at 137 forms the beamformer output z[l]. An inverse DFT 138 transforms the beamformer output back to the time domain where a time-gating window is applied at 139. Finally, the time-gated signal energy is calculated at 140, resulting in the backscatter strength assigned to location $r_0$ in the image.

For design purposes we assume that the received signal in the $i^{th}$ channel contains only the backscatter due to a lesion at location $r_0$. Let this received signal after skin-breast artifact removal be denoted by $x_i[n]$ and its DFT denoted $$X_i[l]=I(\omega_l)S_{ii}(r_0,\omega_l), 1 \leq i \leq M, 1 \leq l \leq N \qquad (37)$$

where $\omega_l$ is the frequency corresponding to the $l^{th}$ DFT index, $I(\omega_l)$ is the DFT of the transmitted pulse and $S_{ii}(r_0,\omega_l)$ is an analytical model of the monostatic frequency response associated with propagation through breast tissue from the $i^{th}$ antenna to the scatterer located at $r_0$ and back. Note that this is the same relation as Eqn. (14) except for the use of discrete frequencies. $I(\omega_l)$ corresponds to $P(\omega)$ in Eqn. (14) and $S_{ii}(r_0,\omega_l)$ corresponds to $V_i(r,\omega)$ in Eqn. (14). This notation is used below to illustrate the beamformer design in the frequency domain. A series of narrowband measurements may be used in place of a single ultrawideband measurement for each antenna location, in which case $I(\omega_l)$ represents the amplitude and phase of the $l^{th}$ transmitted sinusoidal signal with carrier frequency $\omega_l$.

As in the time domain design, we delay the signal $x_i[n]$ at 130 by an integer number of samples $n_i(r_0)=n_a-\tau_i(r_0)$ so that the waveforms in each channel are approximately aligned in time. Here $n_a$ is the reference sample interval to which all received signals are aligned and $\tau_i(r_0)$ denotes the round-trip propagation delay for location $r_0$ in the $i^{th}$ channel in units of sample intervals. The delay is computed by dividing the round-trip path length by the average speed of propagation and rounding to the nearest sample. We choose $n_a$ as the worst case delay over all channels and locations, that is, $$n_a = \max_{i,r_0} \tau_i(r_0) \qquad (38)$$

The time-aligned signals are windowed at 132 before the filtering stage to remove interference and clutter that is present prior to time $n_a$ using the window function $$g[n] = \begin{cases} 1 & n \geq n_a \\ 0 & \text{otherwise} \end{cases} \qquad (39)$$

At this stage the signals are transformed to the frequency domain at 134 and passed through the beamformer at 135. The purpose of beamforming is to equalize the transmitted pulse, equalize path-length dependent dispersion and attenuation, interpolate any fractional time delays, and perform spatial discrimination against clutter. The beamformer weight in the $i^{th}$ channel at DFT frequency index l is denoted as $W_i[l]$. We design the beamformer using the minimum number of coefficients or equivalently the minimum number of design frequencies. The minimum number of frequency-domain MIST beamformer coefficients, L, may be determined as follows. The maximum distance of any point in the scan region from the antennas determines the time extent of interest for the received signal, and consequently determines the minimum DFT length, N. The DFT length, N, and the sampling frequency, $\omega_s$, determine the spacing between the DFT frequencies as $\Delta\omega=\omega_s/N$. If the bandwidth of interest is B, then the minimum number of frequencies that must be considered in the beamformer design is given by $$L = \left[\frac{B}{\Delta\omega}\right] = \left[\frac{BN}{\omega_s}\right] \qquad (40)$$

We assume that the band of interest corresponds to the set of L frequencies, $\{\omega_l : l_0 \leq l \leq l_0+L-1\}$.

In order for the beamformer to compensate for the transmitted pulse and propagation to and from location $r_0$, we require the output to have unit gain and linear phase as shown by $$I(\omega_l)\sum_{i=1}^{M} S_{ii}(r_0, \omega_l)e^{-j\omega_l n_i(r_0)T_s} W_i^*[l] = I(\omega_l)\sum_{i=1}^{M} \tilde{S}_{ii}(r_0, \omega_l)e^{-j\omega_l \tau_i(r_0)T_s} e^{-j\omega_l n_i(r_0)T_s} W_i^*[l]$$

$$= e^{-j\omega_l(\tau_0+n_a)T_s}, l_0 \leq l \leq l_0+L-1 \qquad (41)$$

Here $$\tilde{S}_{ii}(r_0, \omega_l)$$

denotes the frequency response due to propagation after removing the linear phase shift associated with round-trip propagation delay, $\tau_i(r_0)$, the value $\tau_0=(N-1)/2$ represents the average time delay introduced by the beamformer, and $T_s$ is the sampling interval. Combining the phase factors associated with the propagation and the time alignment according to $n_a=\tau_i(r_0)+n_t(r_0)$, we obtain the design constraints on $W_i[l]$ as $$I(\omega_l)\sum_{i=1}^{M}\tilde{S}_{ii}(r_0,\omega_l)W_i^*[l] = e^{-j\omega_l\tau_0 T_s}, l_0 \le l \le l_0+L-1 \quad (42)$$

Stack the $W_i[l]$ and $$\tilde{S}_{ii}(r_0,\omega_l)$$

to form the M×1 vectors $$\tilde{S}(r_0,\omega_l) = I(\omega_l)[\tilde{S}_{ii}(r_0,\omega_l)\tilde{S}_{22}(r_0,\omega_l)\ldots\tilde{S}_{MM}(r_0,\omega_l)]^T \quad (43)$$

$$W[l]=[W_1[l]W_2[l]\ldots W_M[l]]^T \quad (44)$$

and rewrite equation (42) in compact form as $$W^H[l]\tilde{S}(r_0,\omega_l) = e^{-j\omega_l\tau_0 T_s}, l_0 \le l \le l_0+L-1 \quad (45)$$

If these constraints are satisfied, then the beamformer output at frequency $\omega_l$ is given by $$Z(\omega_l)=e^{-j\omega_l(\tau_0+n_a)T_s} l_0 \le l \le l_0+L-1 \quad (46)$$

The beamformer output is converted back to a time-domain signal, z[n], using an inverse DFT at 138 and a window, $h[r_0,n]$, is applied at 139 to eliminate additional clutter. The output energy at this scan location, $p(r_0)$, is obtained at 140 from the sum of the squares of the windowed signal $$p(r_0) = \sum_n |z[n]h[r_0,n]|^2 \quad (47)$$

The reconstructed image of microwave scattering strength is obtained by scanning $r_0$ throughout the reconstruction region and plotting beamformer output energy as a function of location.

The following subsections describe details specific to the design of the filter weights W[l] and the design of the window $h[r_0,n]$.

Beamformer Design

Designing the beamformer in the frequency domain has the advantage of yielding an exact solution to Eqn. (45) which can be expressed in closed-form:

$$W[l] = \frac{\tilde{S}(r_0,\omega_l)e^{j\omega_l\tau_0 T_s}}{\tilde{S}^H(r_0,\omega_l)\tilde{S}(r_0,\omega_l)} \quad (48)$$

This solution is especially appealing in comparison to the time-domain approach since it requires no matrix inversion.

However, the exact solution is not robust because the magnitude of the beamformer weights can become very large when $$\tilde{S}^H(r_0,\omega_l)\tilde{S}(r_0,\omega_l)$$

is small. This is particularly problematic at higher frequencies and deeper scan locations where attenuation results in small values for $S_{ii}(r_0,\omega_l)$. The robustness of a beamformer to errors between actual and assumed propagation models and to background noise is proportional to the norm of the weight vector or noise gain. Using Eqn. (48), we have the noise gain $$G_{ls}[l] = W^H[l]W[l] = \frac{1}{\tilde{S}^H(r_0,\omega_l)\tilde{S}(r_0,\omega_l)} = \frac{1}{\sum_{j=1}^{M}|\tilde{S}_{jj}(r_0,\omega_l)|^2} \quad (49)$$

where the subscript ls refers to the least squares (exact) solution for W[l]. Thus, the noise gain of the exact solution can become arbitrarily large as $$|\tilde{S}_{jj}(r_0,\omega_l)|$$

decreases.

In order to control the noise gain and obtain a robust beamformer, we consider the penalized least squares problem $$W[l] = \underset{W[l]}{\arg\min}\left[\left|W^H[l]\tilde{S}(r_0,\omega_l) - e^{-j\omega_l\tau_0 T_s}\right|^2 + \sum_{i=1}^{M}\lambda_i[l]|W_i[l]|^2\right] \quad (50)$$

where the first term is the approximation error, the second term is the penalty function, and $\lambda_i[l]$, the penalty weight, is selected to trade the norm of $W_i[l]$ against the approximation error. Defining $\Lambda[l]$ as an M×M diagonal matrix with elements $\{\lambda_1[l],\lambda_2[l],\ldots,\lambda_M[l]\}$, the solution to Eqn. (50) may be written as $$W[l] = \frac{\Lambda^{-1}[l]\tilde{S}(r_0,\omega_l)e^{j\omega_l\tau_0 T_s}}{1+\tilde{S}^H(r_0,\omega_l)\Lambda^{-1}[l]\tilde{S}(r_0,\omega_l)} \quad (51)$$

Note that as $\lambda_i[l]$ decreases the approximation error decreases but the norm of $W_i[l]$ increases. In order to compromise between these effects, we select the penalty weights $$\lambda_i[l] = |\tilde{S}_{ii}(r_0,\omega_l)|.$$

With this choice the beamformer coefficients simplify to $$W_i[l] = \frac{\tilde{S}_{ii}(r_0,\omega_l)e^{j\omega_l\tau_0 T_s}}{|\tilde{S}_{ii}(r_0,\omega_l)|\left(1+\sum_{j=1}^{M}|\tilde{S}_{jj}(r_0,\omega_l)|\right)} \quad (52)$$

This solution for the beamformer weights does not require matrix inversion.

We may compare the approximation error and noise gain of this penalized least squares beamformer of Eqn. (52) to those of the unconstrained beamformer in Eqn. (48). The approximation error of Eqn. (48) is zero and its noise gain is given by Eqn. (49). For the beamformer of Eqn. (52), the approximation error is given by $$E_{pls}[l] = |W^H[l]\tilde{S}(r_0, \omega_l) - e^{-j\omega l \tau_0 T_s}|^2 = \frac{1}{\left(1 + \sum_{j=1}^{M} |\tilde{S}_{jj}(r_0, \omega_l)|\right)^2} \quad (53)$$

and the noise gain is $$G_{pls}[l] = W^H[l]W[l] = \frac{M}{\left(1 + \sum_{j=1}^{M} |\tilde{S}_{jj}(r_0, \omega_l)|\right)^2} = M E_{pls}[l] \quad$$

where the subscript pls refers to the penalized least squares solution for W[l]. Comparison of Eqn. (49) and Eqn. (54) reveals that $1/MG_{pls}[l] \leq G_{ls}[l]$. Furthermore, Eqn. (49) indicates that the noise gain of the penalized least squares beamformer cannot exceed M.

Window Design

If the beamformer satisfies Eqn. (45) and the lesion is a point scatterer, then the output z[n] is a time-shifted, attenuated and sampled version of a bandlimited impulse. If the values of $Z(\omega_l)$ outside the band of interest are set to zero, then z[n] has a sinc function envelope and the majority of backscattered energy is contained within the mainlobe. Since both the time shift and bandwidth are known, the location and width of the mainlobe are also known. If the mainlobe occupies time points $n_h$ through $n_h+l_h$ in z[n], then a natural choice for the window is $$h[r_0, n] = \begin{cases} 1 & n_h \leq n \leq n_h + l_h \\ 0 & \text{otherwise} \end{cases} \quad (55)$$

This choice reduces clutter effects by ensuring that the output energy of Eqn. (47) is calculated using only samples of z[n] containing backscattering lesion energy.

In practice, scattering from the tumor is frequency-dependent, so the beamformer output corresponds to the impulse response of the tumor on the band of interest. These dispersive effects increase the duration of the beamformer output and complicate window selection. Our preliminary investigations suggest that the extent of the increase in duration is directly proportional to the tumor size. Since we are interested in detecting very small lesions, we have chosen to design $h[r_0,n]$ assuming a point scatterer model. This gives the largest possible signal-to-clutter ratio (S/C) for small tumors. The S/C for large tumors is reduced by this choice; however, the backscattered signal from larger tumors is much stronger so a compromised S/C is relatively inconsequential for tumor detection.

Example of a 2-D Space-Time Beamformer Design

In order to illustrate the MIST beamforming algorithm presented above, we discuss the frequency-domain design of a 2-D space-time beamformer. For ease of presentation, we show only the 2-D case, but these techniques are directly applicable in three-dimensions (3-D).

Frequency-dependent propagation effects are incorporated into the design of the space-time beamformer via a monostatic transfer function, $S_{ii}(r,\omega)$, which relates the received signal at the $i^{th}$ antenna at location $r_i$ to the transmitted signal at the $i^{th}$ antenna due to a scatterer located at r. In our 2-D example, we assume that each antenna is an infinite line source of electric current, $I(\omega)$, located at $r_i$ in a uniform medium of normal breast tissue. The scatterer is treated as a conducting circular cylinder of infinitesimal radius and infinite length. For this scenario, we use the following transfer function:

$$S_{ii}(r, \omega) = \left[\frac{1}{|r-r_i|^{\frac{1}{2}}} e^{-\alpha(\omega)|r-r_i|} e^{-j\beta(\omega)|r-r_i|}\right]^2 \quad (56)$$

where $\alpha(\omega)$ is the frequency dependent attenuation constant and $\beta(\omega)$ is the frequency dependent phase constant.

The 2-D beamformer is designed for a rigid 1-D conformal antenna array. The array contains 17 elements spanning 8 cm horizontally along the surface of the breast at known locations. The 2-D place that the beamformer is designed to scan spans 10 cm and is 4 cm deep. The transmitted UWB pulse is a differentiated Gaussian with a full width at half maximum equal to 110 ps. Its spectrum has a peak near 6 GHz and significant energy between 1 and 11 GHz.

We design the frequency-domain beamformer over the band 0.5 to 12 GHz and apply a raised cosine taper over the intervals 0.5 to 1 GHz and 11 to 12 GHz to smooth the transition between passband and stopbands. The sampling frequency, $f_s$, is 50 GHz and the maximum round-trip distance between any antenna and the deepest scan location is 24 cm which corresponds to a time interval of $n_a=125$ sampling intervals. Thus N=125 is the data record length and L=28 frequencies are employed to span the band of interest. The design location r is scanned over the breast region using a grid resolution of 1 mm. The post-beamformer window described by (19) is three sampling intervals in length, spanning 60 ps.

After applying the skin-breast artifact removal algorithm to the simulated data, the space-time beamformer is applied to each scan location in the breast. The signal energy is approximated by steering the beamformer to the center location of a 2-mm-diameter tumor, applying windows of varying length to the beamformer output, and calculating the output energy. Similarly, the clutter energy is computed by applying the same process to backscatter waveforms obtained from a tumor-free model, repeating for each scan location within the central 6 cm×2 cm region of the breast, and averaging the results. We choose a window length of three samples (60 ns) in order to balance the goal of maximizing S/C with the goal of maintaining robustness to dispersion. A larger window would capture more signal energy at this scan location, but that same window would capture more clutter energy when the beamformer is steered elsewhere in the breast. The goal of preserving signal energy while discriminating against clutter suggests this strategy of optimizing S/C rather than signal energy alone.

Transmitted Microwave Focussing

Figure 12:
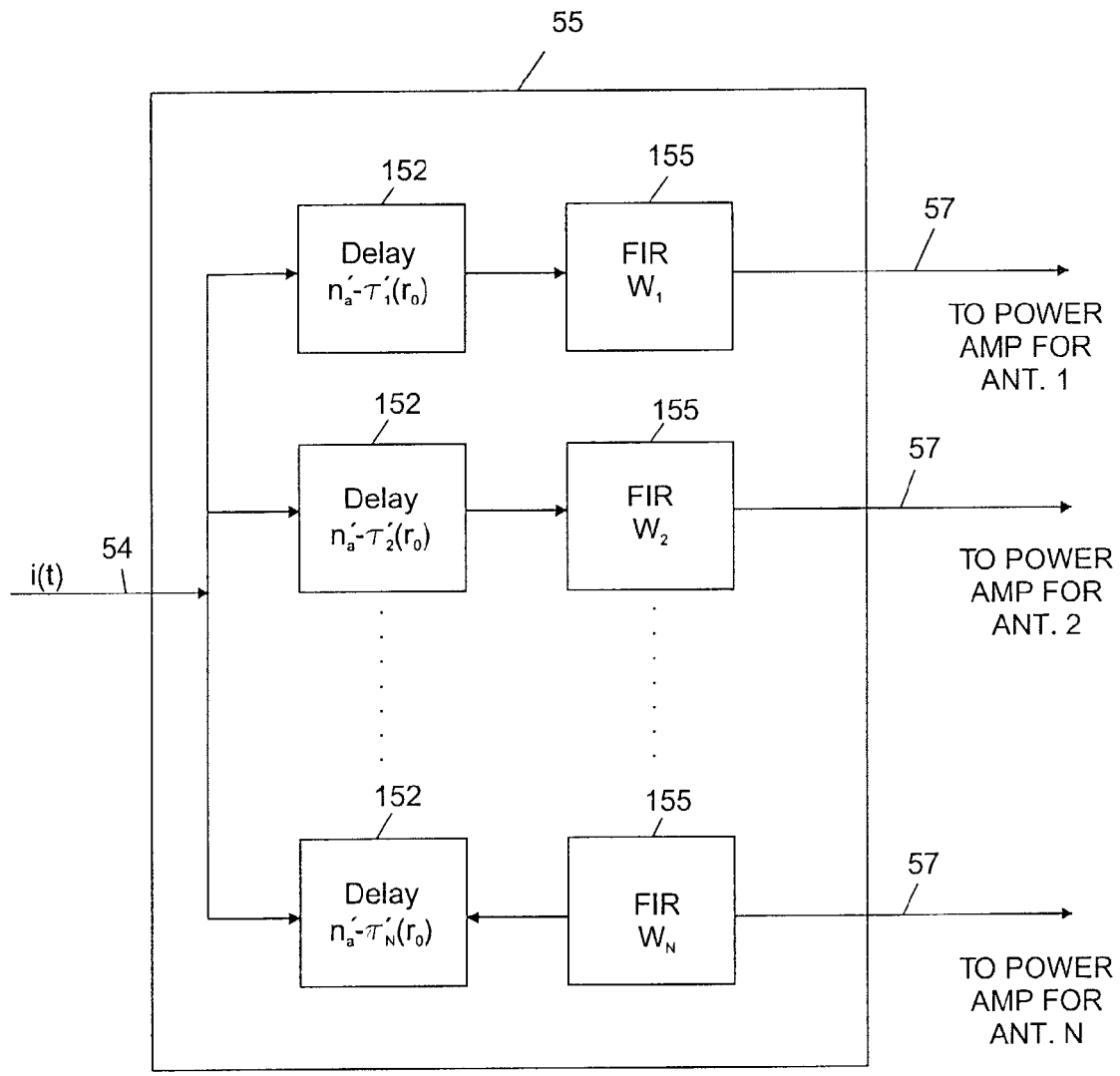
FIG. 12 is a block diagram for transmission of microwave pulses from an array of antennas to focus the microwaves at a chosen location, and which may be utilized in hyperthermia treatment of tumors.

As indicated above, the transmitted microwave energy from the antennas may be focussed at a chosen location for purposes such as increasing the signal-to-clutter ratio and (at sufficiently high energies) hyperthermia treatment of a tumor that has been located as described above. The appropriate timing and shaping of the pulses from the various antennas may be carried out in the signal processing circuitry 55 of a system as shown in FIG. 2. The configuration of the signal processing circuitry 55 for this purpose (which may be implemented in a digital signal processor) is illustrated in FIG. 12. The microwave pulses from the signal generator 51 are provided on the lines 54 to a time delay unit 152 for each of the N antennas 63 in the array 64. The outputs of the delay units 152 are provided to FIR filters 155, and the filtered signals are provided on the lines 57 to the power amplifiers 58. The following describes the design of the delays 152 and filters 155.

Let the propagation model from the $i^{th}$ antenna 63 to the hypothesized tumor location $(r_0)$ be $V_i'(r_0,\omega)$ and $\tau_i'(r_0)$ be the one-way propagation delay. As before, we choose $n_a'$ as the worst case delay over all channels, that is, $$n_a' = \left(\max_i \tau_i(r_0)\right).$$

Assume $\tau_i'(r_0)$ is rounded to the nearest integer of samples.

Let $\tilde{V}_i'(r_0, \omega) = V_i'(r_0, \omega) = V_i'(r_0, \omega)e^{j\omega\tau_1'(r_0)}$.

Writing $W_i(\omega)=W_i^T d(\omega)$ as in Eqn. (17), the design equations for the FIR filters 155 are $$\sum_{i=1}^{N} \tilde{V}_i'(r_0, \omega) w_i^T d(\omega) \approx e^{-j\omega T_s(L-1)/2}$$

which is analogous to Eqn. (19). Solve this as in Eqn. (28) (penalized least squares sense), with the obvious changes to Eqn. (22).

We may pick the tumor location from the peak of the image. In the presence of errors between the assumed propagation model $V_i'(r_0,\omega)$ and the true one, it is probably best to choose the peak from an image generated by transmitting from the center antenna and receiving at all antennas, since then the difference between propagation paths to each antenna is the one-way trip (the trip from antenna to tumor is the same in all receive channels). In this way, errors in the propagation model that lead to localization errors should be approximately compensated.

Images generated by MIST beamforming do not uniquely determine the exact tumor configuration in the breast. Deducing the tumor configuration from the energy plots does not have a unique solution because different tumor configurations could lead to qualitatively similar energy plots. If, however, on the assumption that at most a single tumor is present then the image does provide insight into tumor properties, such as size.

The foregoing examples of beamformers were designed for the actual average dielectric properties of the normal breast tissue present in the model. In practice, these properties will vary from patient to patient within a certain margin, and exact normal breast tissue properties will be unknown. The frequency-domain design is nonetheless robust with respect to potential mismatch between the assumed and the actual dielectric properties averages.

It is understood that the invention is not limited to the embodiments set forth herein for purposes of illustrating the invention, but embraces all such forms thereof as come within the scope of the following claims.

What is claimed is:

1. A space-time microwave imaging system for imaging an object comprising:
    (a) an array of antennas for radiating and receiving microwaves;
    (b) a microwave pulse source connected to the array of antennas to provide pulse signals to the antennas;
    (c) a receiver connected to the antennas to detect the microwave signals received by the antennas and provide signal data corresponding thereto; and
    (d) a computer connected to receive the signal data, the computer programmed to estimate an artifact reflection component of the signal at each antenna as a filtered combination of the signals at all other antennas and to subtract the estimated artifact reflection component from the signal data to provide corrected signal data, with weights of the filters chosen to minimize the residual signal over that portion of the received data dominated by the reflection, and the computer further programmed to process the corrected signal data in a beamformer process to time shift the corrected signal data to approximately align the returns from a scatterer at a candidate location, to pass the time aligned signals through a bank of filters with a filter for each antenna, to sum the outputs of the filters to form a summed signal, and to calculate the power in the summed signal to produce a beamformer output signal, wherein the beamformer filters are designed to present maximum gain to scattered signals originating from the candidate location, and to scan the beamformer process to a plurality of different candidate locations in the object to be imaged by changing the time shifts and filter weights to generate multi-dimensional output power data.

2. The imaging system of claim 1 including an output device connected to the computer to display the multi-dimensional output power data as a function of scanned locations.

3. The imaging system of claim 1 wherein the computer is further programmed to time gate the summed signal to form a time gated summed signal and to calculate the power in the time gated summed signal, and to scan the beamformer process to a plurality of different candidate locations in the object to be imaged by changing the time shifts, filter weights and time gates to generate multi-dimensional output power data.

4. The imaging system of claim 3 wherein the computer is further programmed to process the beamformer output signal from the filters prior to time gating using a parametric signal processing model to compensate frequency dependent scattering effects.

5. The imaging system of claim 1 wherein the microwave pulse source provides pulses having pulse widths on the order of 100 picoseconds or less in duration.

6. The imaging system of claim 1 wherein the microwave pulse source is connected to the antennas to provide pulse signals to one antenna at a time.

7. The imaging system of claim 1 wherein the microwave pulse source is connected to the antennas to provide pulse signals to all of the antennas simultaneously.

8. The imaging system of claim 1 wherein the computer is programmed in the beamformer process to apply a selected window to the time aligned signals before passing the time aligned signals through the bank of filters, and further to apply a selected window to the summed signal before the power in the summed signal is calculated.

9. The imaging system of claim 1 wherein the computer is programmed to calculate the power at each candidate location as the sum of the squares of each sample of the summed signal.

10. The imaging system of claim 1 wherein the beamformer filters are finite-impulse response filters designed to satisfy a penalized least squares condition to present unit gain to scattered signals originating from a candidate location.

11. The imaging system of claim 1 further including signal processing circuitry that receives the pulses from the source and passes the pulses through a delay and a filter for each antenna before providing the delayed and filtered pulses to the antennas, the delays and filters selected to focus the radiated microwave energy from the array of antennas at a selected candidate location in the object.

12. A method of carrying out space-time microwave imaging of an individual comprising:
  (a) transmitting microwave signals from a plurality of antenna locations into an individual to be examined;
  (b) receiving backscattered microwave signals at a plurality of antenna locations to provide received signals from the plurality of antenna locations;
  (c) processing the received signals in a computer in a beamformer process by time shifting the received signal data to approximately align the returns from a scatterer at a candidate location, passing the time aligned signals through a bank of filters with a filter for each antenna location, summing the outputs of the filters to provide a summed signal, and equalizing the summed signal to reduce a sensitivity to a time-gate duration; and time-gating the equalized signal to provide a time-gated signal, and calculating the power in the time-gated signal to produce a beamformer output signal, wherein the filters are designed to present maximum gain to scattered signals originating from the candidate location; and
  (d) then scanning the beamformer process to a plurality of different candidate locations in the individual and repeating steps (a), (b) and (c) at each candidate location by changing the time shifts, filter weights and time gates for each candidate location to generate multi-dimensional output power data.

13. The method of claim 12 wherein the step of transmitting microwave signals comprises transmitting microwave pulses having pulse widths on the order of 100 picoseconds or less in duration.

14. The method of claim 12 wherein the step of transmitting microwave signals comprises transmitting microwave pulses having frequency content at 10 GHz or higher.

15. The method of claim 12 wherein the step of filtering is carried out in the time domain.

16. The method of claim 12 wherein the step of filtering is carried out in the frequency domain.

17. The method of claim 16 wherein the step of filtering in the frequency domain is carried out for each signal from an antenna location in a channel by performing a fast Fourier transform on the signal data to provide frequency domain data, applying weights to the frequency domain data in each channel and adding the weighted data; and then performing an inverse fast Fourier transform on the weighted data to provide a filtered time domain data signal.

18. The method of claim 12 including compensating the received signal data for frequency dependent scattering before carrying out beamformer processing.

19. The method of claim 12 including transmitting the microwave signals from an array of antennas so as to focus the microwave power on a candidate location.

20. The method of claim 12 further including, before the step of processing the received signals in a beamformer process, the step of:
  carrying out an artifact response subtraction process on the received signals in the computer by estimating the interface reflection component of the signal at each antenna location as a combination of the received signals at the other antenna locations passed through filters to provide corrected signal data, the filters having weights chosen to minimize the received signal over that portion of the received signal dominated by the artifact response, and providing the corrected signal data to the beamformer process.

21. The method of claim 12 wherein microwave signals are provided to one antenna at a time and backscattered microwave signals are received from one antenna at a time for each of the antenna locations.

22. The method of claim 12 wherein microwave signals are transmitted from all of the antennas simultaneously and backscattered microwave signals are received from all of the antennas simultaneously.

23. The method of claim 12 including in the beamformer process the steps of applying a selected window to the time aligned signals before filtering the signals and further applying a selected window to the summed signal before calculating the power in the summed signal.

24. The method of claim 12 wherein the power is calculated at each candidate location as the sum of the squares of each sample of the summed signal.

25. The method of claim 12 wherein filtering is carried out utilizing finite-impulse response filters designed to satisfy a penalized least squares condition to present unit gain to scattered signals originating from a candidate location.

26. The method of claim 12 wherein the step of transmitting the microwave signals is carried out simultaneously from all of the antenna locations by passing microwave pulses for each antenna at an antenna location through a delay and a filter for each antenna, the delays and filters selected to focus the radiated microwave energy from the antennas at a selected candidate location in the object.

27. A method of compensating for an artifact reflection in microwave imaging of an individual comprising:
  (a) transmitting microwave signals from a plurality of antenna locations into an individual to be examined;
  (b) receiving backscattered microwave signals at a plurality of antenna locations to provide received signals from the plurality of antenna locations;
  (c) carrying out an artifact response subtraction process on the received signals in a computer by estimating the artifact reflection component of the signal at each antenna location as a combination of the received signals at the other antenna locations passed through filters to provide corrected signal data, the filters having weights chosen to minimize the received signal over that portion of the received signal dominated by the artifact response; and
  (d) compensating the corrected signal data for frequency dependent scattering.

28. The method of claim 27 wherein the step of transmitting microwave signals comprises transmitting microwave pulses having pulse widths on the order of 100 picoseconds or less in duration.

29. The method of claim 27 wherein the step of transmitting microwave signals comprises transmitting microwave pulses having frequency content at 10 GHz or higher.

30. The method of claim 27 including transmitting the microwave signals from an array of antennas so as to focus the microwave power on a candidate location.

31. A method of carrying out space-time microwave imaging of an individual comprising:
(a) transmitting microwave signals from a plurality of antenna locations into an individual to be examined;
(b) receiving backscattered microwave signals at a plurality of antenna locations to provide received signals from the plurality of antenna locations;
(c) carrying out an artifact response subtraction process on the received signals in the computer by estimating the artifact reflection component of the signal at each antenna location as a combination of the received signals at the other antenna locations passed through filters to provide corrected signal data, the filter weights chosen to minimize the received signal over that portion of the received signal dominated by the artifact response;
(d) processing the corrected signal data in a computer in a beamformer process by time shifting the received signal data to approximately align the returns from a scatterer at a candidate location, passing the time aligned signals through a bank of filters with one filter in each channel, summing the outputs of the filters to provide a summed signal, and time-gating the summed signal to provide a time-gated signal, and calculating the power in the time-gated signal to produce a beamformer output signal, wherein the filters are designed to present maximum gain to scattered signals originating from the candidate location; and
(e) then scanning the beamformer process to a plurality of different candidate locations in the individual and repeating steps (a), (b) (c) and (d) at each candidate location by changing the time shifts, filter weights and time gates for each candidate location to generate multi-dimensional output power data.

32. The method of claim 31 wherein the step of transmitting microwave signals comprises transmitting microwave pulses having pulse widths on the order of 100 picoseconds or less in duration.

33. The method of claim 31 wherein the step of transmitting microwave signals comprises transmitting microwave pulses having frequency content at 10 GHz or higher.

34. The method of claim 31 wherein the step of filtering is carried out in the time domain.

35. The method of claim 31 wherein the step of filtering is carried out in the frequency domain.

36. The method of claim 35 wherein the step of filtering in the frequency domain is carried out for each signal from an antenna location in a channel by performing a fast Fourier transform on the signal data to provide frequency domain data, applying weights to the frequency domain data in each channel and adding the weighted data; and then performing an inverse fast Fourier transform on the weighted data to provide a filtered time domain data signal.

37. The method of claim 31 including compensating the received signal data for frequency dependent scattering before carrying out beamformer processing.

38. The method of claim 31 including transmitting the microwave signals from an array of antennas so as to focus the microwave power on a candidate location.

39. The method of claim 31 wherein microwave signals are provided to one antenna at a time and backscattered microwave signals are received from one antenna at a time for each of the antenna locations.

40. The method of claim 31 wherein microwave signals are transmitted from all of the antennas simultaneously and backscattered microwave signals arc received from all of the antennas simultaneously.

41. The method of claim 31 including in the beamformer process the steps of applying a selected window to the time aligned signals before filtering the signals and further applying a selected window to the summed signal before calculating the power in the summed signal.

42. The method of claim 31 wherein the power is calculated at each candidate location as the sum of the squares of each sample of the summed signal.

43. The method of claim 31 wherein filtering is carried out utilizing finite-impulse response filters designed to satisfy a penalized least squares condition to present unit gain to scattered signals originating from a candidate location.

44. The method of claim 31 wherein the step of transmitting the microwave signals is carried out simultaneously from all of the antenna locations by passing microwave pulses for each antenna at an antenna location through a delay and a Filter for each antenna, the delays and filters selected to focus the radiated microwave energy from the antennas at a selected candidate location in the object.

45. An artifact reflection compensation system for use in space-time microwave imaging comprising:
(a) an array of antennas for radiating and receiving microwaves;
(b) a microwave pulse source connected to the array of antennas to provide pulse signals to the antennas;
(c) a receiver connected to the antennas to detect the microwave signals received by the antennas and provide signal data corresponding thereto; and
(d) a computer connected to receive the signal data, the computer programmed to estimate an artifact reflection component of the signal at each antenna as a filtered combination of the signals at all other antennas, to subtract the estimated artifact reflection component from the signal data to provide corrected signal data, and to compensate the corrected signal data for frequency dependent scattering.

46. The system of claim 45 wherein the microwave pulse source provides pulses having pulse widths on the order of 100 picoseconds or less.

* * * * *

UNITED STATES PATENT AND TRADEMARK OFFICE
CERTIFICATE OF CORRECTION

PATENT NO. : 7,570,063 B2
APPLICATION NO. : 10/190352
DATED : August 4, 2009
INVENTOR(S) : Van Veen et al.

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by (1196) days Delete the phrase "by 1196 days" and insert -- by 1865 days --

Signed and Sealed this

Twenty-fourth Day of August, 2010

David J. Kappos
*Director of the United States Patent and Trademark Office*